United States Patent
Cai et al.

(10) Patent No.: US 9,102,631 B2
(45) Date of Patent: Aug. 11, 2015

(54) 1-(ARYLMETHYL)-5,6,7,8-TETRAHYDRO-QUINAZOLINE-2,4-DIONES AND ANALOGS AND THE USE THEREOF

(71) Applicant: Impact Therapeutics, Inc., Nanjing, Jiangsu (CN)

(72) Inventors: Suixiong Cai, Jiangsu (CN); Ye Edward Tian, Jiangsu (CN); Lizhen Wu, Jiangsu (CN); Lijun Liu, Jiangsu (CN); Xiaozhu Wang, Jiangsu (CN); Yangzhen Jiang, Jiangsu (CN); Guoxiang Wang, Jiangsu (CN); Xiuyan Zhang, Jiangsu (CN); Qingbing Xu, Jiangsu (CN); Zheng Meng, Jiangsu (CN)

(73) Assignee: IMPACT Therapeutics, Inc., Nanjing, Jiangsu (CN)

( * ) Notice: Subject to any disclaimer, the term of this patent is extended or adjusted under 35 U.S.C. 154(b) by 0 days.

(21) Appl. No.: 14/355,071

(22) PCT Filed: Nov. 1, 2012

(86) PCT No.: PCT/CN2012/083914
§ 371 (c)(1),
(2) Date: Apr. 29, 2014

(87) PCT Pub. No.: WO2013/064083
PCT Pub. Date: May 10, 2013

(65) Prior Publication Data
US 2014/0275711 A1 Sep. 18, 2014

(30) Foreign Application Priority Data

Nov. 1, 2011 (CN) .......................... 2011 1 0340698

(51) Int. Cl.
| | |
|---|---|
| C07D 239/96 | (2006.01) |
| C07D 401/12 | (2006.01) |
| C07D 403/12 | (2006.01) |
| C07D 409/12 | (2006.01) |
| C07D 417/12 | (2006.01) |
| A61K 31/517 | (2006.01) |
| C07D 239/90 | (2006.01) |
| C07D 487/04 | (2006.01) |
| C07D 491/052 | (2006.01) |
| C07D 495/04 | (2006.01) |
| A61K 45/06 | (2006.01) |
| C07D 405/12 | (2006.01) |
| C07D 239/70 | (2006.01) |
| A61N 5/10 | (2006.01) |
| C07D 409/14 | (2006.01) |

(52) U.S. Cl.
CPC ............ *C07D 239/96* (2013.01); *A61K 31/517* (2013.01); *A61K 45/06* (2013.01); *A61N 5/10* (2013.01); *C07D 239/70* (2013.01); *C07D 239/90* (2013.01); *C07D 401/12* (2013.01); *C07D 403/12* (2013.01); *C07D 405/12* (2013.01); *C07D 409/12* (2013.01); *C07D 409/14* (2013.01); *C07D 417/12* (2013.01); *C07D 487/04* (2013.01); *C07D 491/052* (2013.01); *C07D 495/04* (2013.01)

(58) Field of Classification Search
CPC .. C07D 239/96; C07D 401/12; C07D 403/12; C07D 409/12; C07D 417/12
See application file for complete search history.

(56) References Cited

U.S. PATENT DOCUMENTS

| | | |
|---|---|---|
| 2014/0023642 A1 | 1/2014 | Cai et al. |
| 2014/0031358 A1 | 1/2014 | Liu et al. |

FOREIGN PATENT DOCUMENTS

| | | |
|---|---|---|
| WO | WO 02/06247 A1 | 1/2002 |
| WO | WO 02/40455 A1 | 3/2002 |
| WO | WO 03/059892 A1 | 7/2003 |

OTHER PUBLICATIONS

International Search Report for International Patent Appl. No. PCT/CN2012/083914, The State Intellectual Property Office, People's Republic of China, mailed Feb. 14, 2013.

*Primary Examiner* — Brian McDowell
(74) *Attorney, Agent, or Firm* — Sterne, Kessler, Goldstein & Fox P.L.L.C.

(57) ABSTRACT

Disclosed are novel 1-(arylmethyl)-5,6,7,8-tetrahydroquinazoline-2,4-diones and analogs thereof, represented by the Formula 1:

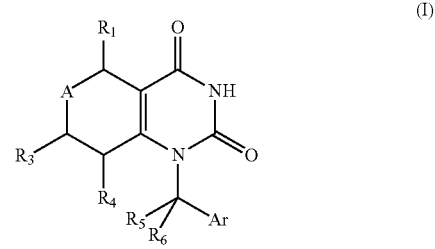

(I)

wherein Ar, A, $R_1$, $R_3$-$R_6$ are defined herein. Compounds having Formula I are PARP inhibitors. Therefore, compounds of the invention may be used to treat clinical conditions that are responsive to the inhibition of PARP activity, such as cancer.

3 Claims, No Drawings

1-(ARYLMETHYL)-5,6,7,8-TETRAHYDRO-QUINAZOLINE-2,4-DIONES AND ANALOGS AND THE USE THEREOF

BACKGROUND OF THE INVENTION

1. Field of the Invention

This invention is in the field of medicinal chemistry. In particular, the invention relates to 1-(arylmethyl)-5,6,7,8-tetrahydroquinazoline-2,4-diones and analogs, and the use of these compounds as poly (ADP-ribose) polymerase (PARP) inhibitors and anti-cancer drugs.

2. Related Art

Poly (ADP-ribose) polymerase (PARP) catalyzes the addition of poly (ADP-ribose) to the target protein using NAD+ that is an important process in DNA repair. This is an essential process for maintaining DNA and chromosome integrity and stability, and for ensuring the survival of mammalian cells. PARP-1 catalyzes the majority of the intracellular ADP-ribose polymerization reactions, although PARP-2 and other subtypes also have this function. The PARP-1 knockout mice do not have the repair function for single-stranded DNA damages (Krishnakumar and Kraus. 2010, Molecular Cell 39:8). Cancer cells with DNA repair defects, such as BRCA1 (breast cancer 1) or BRCA2 (breast cancer 2) deficiency, are particularly sensitive to DNA damaging anticancer agents, including platinum chemotherapy drugs, DNA methylation anticancer drugs and DNA topoisomerase inhibitors, or radiation therapy. Phase II clinical trial data have shown that PARP-1 inhibitor olaparib (AZD2281) was effective for the treatment of advanced breast cancer (Andrew Tutt et al., 2009, J. Clin. Oncol 27:18 s; Andrew Tutt et al., 2010 Lancet 376:235; RA Dent et al., 2010 J. Clin. Oncol. 28:15 s). These scientific and clinical results demonstrated that PARP-1 inhibitors may be used as effective anti-cancer drugs to treat a variety of cancers. The applications of PARP-1 inhibitors for the treatment of cancer are mainly based on two mechanisms. First, because of the rapid growth, DNA replication is much higher in cancer cells than in normal cells. Drugs that cause DNA damage will induce cancer cell death selectively. However, due to the presence of DNA repair enzymes, the therapeutic effects of these drugs cannot be fully materialized. By inhibiting the DNA repair mechanism, PARP-1 inhibitors in combination with commonly used DNA damaging anti-cancer drugs, such as temozolomide, can achieve synergy effects and greatly enhance the anticancer effects of currently used anticancer drugs. Second, for cancer cells with DNA repair deficiency, such as BRCA1 or BRCA2 deficient triple-negative breast cancer, PARP-1 inhibitors can directly kill the cancer cells and function as anticancer drugs independently. According to statistics, about 10-15% of breast cancer patients have family history of genetic factors, in which the BRCA1 or BRCA2 gene mutations account for 15-20% of all hereditary breast cancers. Since PARP-1 is involved in DNA repair, utilization of PARP-1 inhibitors to inhibit DNA repair may be an effective and selective treatment for cancers with DNA repair genetic defect, including triple-negative breast cancers. Furthermore, PARP-1 inhibitors may also be used to treat diseases due to excessive cell death, including central nervous system diseases such as stroke and neurodegenerative diseases (Akinori Iwashita et al., 2004, J. Pharmacol. Exp. Thera. 310: 425).

The inhibitory activity of PARP-1 inhibitors can be measured by directly using PARP-1 enzymes. In addition, since PARP-1 inhibitors can increase the cytotoxicity of DNA damaging anti-cancer drugs such as methyl mathanesulfonate (MMS) on cancer cells, the activity of PARP-1 inhibitors can also be determined by measuring cell viability, such as using a MTT assay, in the presence of DNA damaging anti-cancer drugs.

It has been known that many cancer chemotherapeutic drugs trigger cancer cells to undergo apoptosis. The mechanism of apoptosis involves the activation of a series of proteolytic enzymes called caspases. Caspases are cysteine-aspartate proteases, a main group of enzymes playing key functions in apoptosis, which generally exist in the cell in the inactive zymogen state. They are specific for the hydrolysis of the peptide bond with aspartic acid residues at the $P_1$ position of substrates. Among these caspases, caspase-3, 6, and 7 are key effector caspases that cleave multiple protein substrates in cells, leading to cell death. Cellular caspase activity can be determined using fluorescent caspase substrates. PARP-1 inhibitors can increase the apoptosis-inducing activity of many DNA damaging anticancer drugs such as MMS. Therefore, the activity of PARP-1 inhibitors can be determined via measuring the intracelluar caspase activity of cancer cells, in the presence DNA damaging anticancer drugs.

WO2003059892 disclosed tetrahydroquinazolinediones and analogs as poly(ADP-ribose) polymerase (PARP) inhibitors, wherein A=CH$_2$, O, S; X=alkylene, which may be replaced by oxygroup; R$_1$=H, alkoxycarbonyl; R$_2$=(un)substituted aryl and heteroaryl, which may be substituted by NO$_2$, halo, CN, etc.

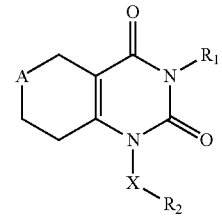

WO2002040455 disclosed the preparation of amidoalkyl uracil derivatives as PARP inhibitors, wherein A=D, CH$_2$D, DCH$_2$, CH:CHCH$_2$, CH$_2$CH:CH, CH$_2$CH$_2$D, DCH$_2$CH$_2$, CH$_2$DCH$_2$; D=CH$_2$, O, S; E, G=substituted alkenyl, cycloalkenyl; T=CH$_2$; U, V=substituted aryl, heteroaryl; W=O, S, CO$_2$, OCO, NR$_4$; R$^4$=H, alkyl; m, n, q, p=0, 1; X=O, S, NR$^5$; R$^5$=H, alkyl, PhCH$_2$; Y$_1$=H; Y$_2$=OH; S; Y$_1$Y$_2$=O, S, NR$^6$; R$^6$=H, alkyl, PhCH$_2$; R$^1$=H, alkyl, halo-substituted cycloalkyl; R$^2$=H, alkoxycarbonyl; R$^3$=substituted aryl, heteroaryl.

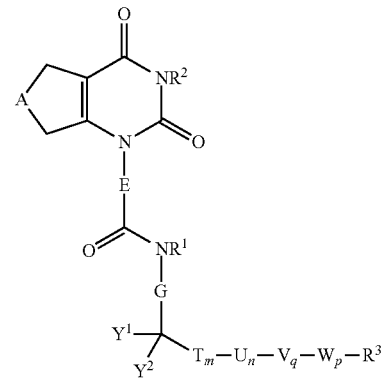

WO2002006247 disclosed the preparation of fused amidoalkyl uracil derivatives as PARP inhibitors, wherein A=D, CH$_2$D, DCH$_2$, CH:CHCH$_2$, CH$_2$CH:CH, CH$_2$CH$_2$D, DCH$_2$CH$_2$, CH$_2$DCH$_2$; D=CH$_2$, O, S; X=substituted alkenyl, cycloalkenyl; R$^1$=H, haloalkyl, cycloalkyl; $R^2=SO_2R^4$, $SO_2NR^5R^6$, $COR^7$, $CONR^8R^9$, $CO_2R^{10}$; substituted alkyl, cycloalkyl, GE; E=substituted aryl, heterocyclic group, G is (un)substituted aryl, heteroaryl; $R^5$, $R^6$=H, substituted cycloalkyl, alkyl, aryl, heteroaryl; or $R^5R^6$=substituted heterocyclic group; $R^7$=substituted alkyl, cycloalkyl; GE (as above); $R^8$, $R^9$=H, substituted alkyl, cycloalkyl; or $R^8R^9$=substituted heteroaryl; $R^{10}$=substituted alkyl, cycloalkyl, aryl; or $R^1R^2$=mono or disubstituted heterocylic group; $R^3$=H, alkoxycarbonyl.

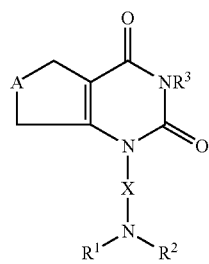

SUMMARY OF THE INVENTION

The invention provides novel 1-(arylmethyl)-5,6,7,8-tetrahydroquinazoline-2,4-diones and analogs, as represented in Formulae I, II and III. These compounds have PARP inhibitory activities.

The present invention also provides pharmaceutical compositions comprising a compound of Formula I, II or III in an effective amount for the treatment of cancer.

The invention also provides a pharmaceutical composition useful for the treatment of cancer, containing an effective amount of a compound of one of the Formula I, II or III in admixture with one or more pharmaceutically acceptable carriers or diluents.

The invention also provides a pharmaceutical composition useful for the treatment of cancer, containing an effective amount of a compound of one of the Formula I, II or III, in combination with one known anticancer drugs or its pharmaceutically acceptable salts.

The invention also is directed to methods for the preparation of novel compounds of Formulae I, II and III.

DETAILED DESCRIPTION OF THE INVENTION

The novel and potent PARP inhibitors of the present invention include 1-(arylmethyl)-5,6,7,8-tetrahydroquinazoline-2,4-diones and analogs, as represented in Formulae I, II and III.

Specifically, compounds of the present invention are represented by Formula I:

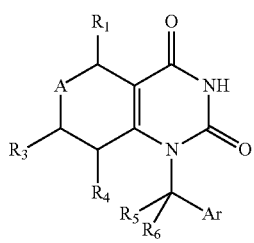

(I)

or pharmaceutically acceptable salts or prodrugs thereof, wherein:

Ar is an optionally substituted aryl or an optionally substituted heteroaryl;

A is $(CHR_2)_n$, O, S or $NR_7$; n=0-3;

$R_1$-$R_6$ independently are hydrogen, halo, optionally substituted amino, optionally substituted alkoxy, optionally substituted $C_{1-10}$alkyl, haloalkyl, alkenyl, alkynyl, nitro, cyano, acylamido, hydroxy, thiol, acyloxy, azido, carboxy, ethylenedioxo, carbonylamido or optionally substituted alkylthiol;

$R_7$ is hydrogen, optionally substituted $C_{1-10}$ alkyl, haloalkyl, alkenyl, alkynyl.

Optionally substituted $C_{1-10}$ alkyl for $R_1$-$R_6$ are groups such as hydroxyalkyl, aminoalkyl, carboxyalkyl, and alkyl substituted by groups defined as follows. Optionally substituted $C_{1-10}$ alkyl for $R_7$ are groups such as hydroxyalkyl, aminoalkyl, carboxyalkyl, and alkyl substituted by groups defined as follows.

Preferred compounds of Formula I include compounds wherein Ar is an optionally substituted phenyl or pyridyl. More preferably, Ar is meta-substituted phenyl or pyridyl. Preferred compounds of Formula I include compounds wherein $R_5$ and $R_6$ are hydrogen. Preferred compounds of Formula I include compounds wherein $R_4$ is hydrogen. Preferred compounds of Formula I include compounds wherein A is $CHR_2$. Preferred compounds of Formula I include compounds wherein B is $CHR_1$ or S.

One group of preferred compounds of the present invention are represented by Formula II:

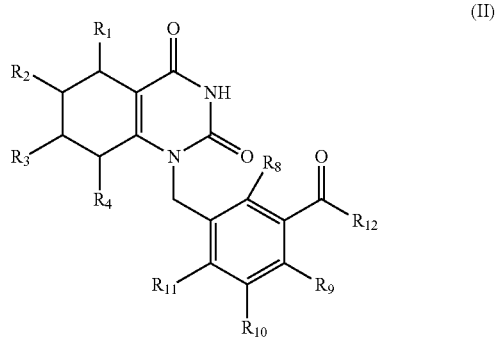

(II)

or pharmaceutically acceptable salts or prodrugs thereof, wherein:

$R_1$-$R_4$ independently are hydrogen, halo, optionally substituted amino, optionally substituted alkoxy, optionally substituted $C_{1-10}$ alkyl, haloalkyl, alkenyl, alkynyl, nitro, cyano, acylamido, hydroxy, thiol, acyloxy, azido, carboxy, carbonylamido or optionally substituted alkylthiol;

$R_8$-$R_{11}$ independently are hydrogen, halo, optionally substituted amino, alkoxy, $C_{1-10}$ alkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamido, aminocarbonyl, hydroxy, thiol, acyloxy, azido, carboxy, carbonylamido, alkylsulfonyl, aminosulfonyl, dialkylaminosulfonyl, alkylsulfiniyl, alkylthiol, or substituted carbonyl;

$R_{12}$ is an optionally substituted amino, alkoxy, $C_{1-10}$ alkyl, haloalkyl, optionally substituted aryl, optionally substituted carbocyclic group, optionally substituted heterocyclic group, optionally substituted heteroaryl, optionally substituted arylalkyl, optionally substituted arylalkenyl, optionally substituted arylalkynyl, optionally substituted heteroarylalkyl, optionally substituted hetcroaylalkenyl, optionally substituted heteroarylalkynyl, optionally substituted carbocycloalkyl, optionally substituted heterocycloalkyl, hydroxyalkyl, hydroxyalkoxy, aminoalkyl, aminoalkoxy, carboxyalkyl, carboxyalkoxy, acylamido, thiol, carbonylamido, alkylsulfonyl, or aminosulfonyl.

One group of preferred compounds of Formula II includes compounds wherein $R_8$ is hydrogen. Another group of preferred compounds of Formula II includes compounds wherein $R_{12}$ is an optionally substituted amino. Another group of preferred compounds of Formula II includes compounds wherein $R_{12}$ is substituted heterocyclic group.

One group of preferred compounds of the present invention are represented by Formula III:

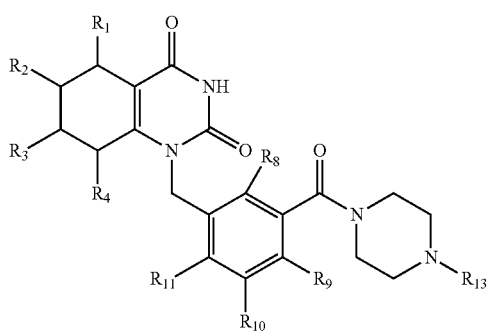

(III)

or pharmaceutically acceptable salts or prodrugs thereof, wherein:
  $R_1$-$R_4$ independently are hydrogen, halo, optionally substituted ammo, optionally substituted alkoxy, optionally substituted $C_{1-10}$ alkyl, haloalkyl, alkenyl, alkynyl, nitro, cyano, acylamido, hydroxy, thiol, acyloxy, azido, carboxy, carbonylamido or optionally substituted alkylthiol;
  $R_8$-$R_{11}$ independently are hydrogen, halo, optionally substituted amino, alkoxy, $C_{1-10}$ alkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamido, aminocarbonyl, hydroxy, thiol, acyloxy, azido, carboxy, carbonylamido, alkylsulfonyl, aminosulfonyl, dialkylaminosulfonyl, alkylsulfiniyl, alkylthiol, or substituted carbonyl;
  $R_{13}$ is an optionally substituted $C_{1-10}$ alkyl, haloalkyl, alkylsulfonyl, optionally substituted benzoyl, alkanoyl, aryl, carbocyclic group, heterocyclic group, heteroaryl, carbocycloalkyl, heterocycloalkyl, hydroxyalkyl, cycloalkylcarbonyl, arylcarbonyl, heteroarylcarbonyl.

Compounds of Formula III includes compounds wherein $R_{13}$ is optionally substituted $C_{1-10}$ alkyl, which includes, without limitation, arylalkyl, heteroarylalkyl, hydroxyalkyl, aminoalkyl, carboxyalkyl, and alkyl substituted by groups defined as follows.

One group of preferred compounds of Formula III includes compounds wherein $R_8$ is hydrogen. Another group of preferred compounds of Formula III includes compounds wherein $R_{13}$ is substituted alkyl, aryl or heteroaryl. Another group of preferred compounds of Formula III includes compounds wherein $R_{13}$ is alkylcarbonyl, cycloalkylcarbonyl, arylcarbonyl, heteroarylcarbonyl.

1-(3-(4-(Pyrimidin-2-yl)piperazine-1-carbonyl)benzy)-5,6,7,8-tetrahydroquinazoline-2,4(1H,3H)-dione;
1-(3-(4-(Cyclopropylcarbonyl)piperazine-1-carbonyl)benzyl)-5,6,7,8-tetrahydroquinazoline-2,4(1H,3H)-dione;
1-(3-(4-(Thiophene-2-carbonyl)piperazine-1-carbonyl)benzyl)-5,6,7,8-tetrahydroquinazol ine-2,4(1H,3H)-dione;
1-(3-(4-(Thiazol-2-yl)piperazine-1-carbonyl)benzyl)-5,6,7,8-tetrahydroquinazoline-2,4(1H,3H)-dione;
1-(3-(4-(Cyclopentylcarbonyl)piperazine-1-carbonyl)benzyl)-5,6,7,8-tetrahydroquinazoline-2,4(1H,3H)-dione;
1-(3-(4-Benzoylpiperazine-1-carbonyl)benzyl)-5,6,7,8-tetrahydroquinazoline-2,4(1H,3H)-dione;
1-(3-(4-(Pyridin-2-yl)piperazine-1-carbonyl)benzyl)-5,6,7,8-tetrahydroquinazoline-2,4(1H,3H)-dione;
1-(3-(4-(Cyclohexylcarbonyl)piperazine-1-carbonyl)benzyl)-5,6,7,8-tetrahydroquinazolin e-2,4(1H,3H)-dione;
1-(3-(4-(Furan-2-carbonyl)piperazine-1-carbonyl)benzyl)-5,6,7,8-tetrahydroquinazoline-2,4(1H,3H)-dione;
1-(3-(4-(Cyclobutylcarbony)piperazine-1-carbonyl)benzyl)-5,6,7,8-tetrahydroquinazoline-2,4(1H, 3H)-dione;
1-(3-(4-(Thiophene-3-carbonyl)piperazine-1-carbonyl)benzyl)-5,6,7,8-tetrahydroquinazol ine-2,4(1H,3H)-dione;
1-(3-(4-(Pyrazin-2-yl)piperazine- 1-carbonyl)benzyl)-5,6,7,8-tetrahydroquinazoline-2,4(1H,3H)-dione;
1-(4-Fluoro-3-(4-benzoylpiperazine-1-carbonyl)benzyl)-5,6,7,8-tetrahydroquinazoline-2,4(1H,3H)-dione;
1-(4-Fluoro-3-(4-(cyclopropylcarbonyl)piperazine-1-carbonyl)benzyl)-5,6,7,8-tetrahydroquinazoline-2,4(1H, 3H)-dione;
1-(4-Fluoro-3-(4-(pyrimidin-2-yl)piperazine-1-carbonyl)benzyl)-5,6,7,8-tetrahydroquinazoline-2,4(1H, 3H)-dione;
1-(4-Fluoro-3-(4-(thiophene-2-carbonyl)piperazine-1-carbonyl)benzyl)-5,6,7,8-tetrahydroquinazoline-2,4(1H,3H)-dione;
1-(4-Fluoro-3-(4-(cyclobutylcarbonyl)piperazine-1-carbonyl)benzyl)-5,6,7,8-tetrahydroquinazoline-2,4(1H, 3H)-dione;
1-(4-Fluoro-3-(4-(thiazol-2-yl)piperazine-1-carbonyl)benzyl)-5,6,7,8-tetrahydroquinazoline-2,4(1H,3H)-dione;
1-(4-Fluoro-3-(4-(cyclohexylcarbonyl)piperazine-1-carbonyl)benzyl)-5,6,7,8-tetrahydroquinazoline-2,4(1H, 3H)-dione:
1-(4-Fluoro-3-(4-(cyclopentylcarbonyl)piperazine- 1-carbonyl)benzyl)-5,6,7,8-tetrahydroquinazoline-2,4(1H, 3H)-dione;
1-(4-Fluoro-3-(4-(pyridin-2-yl)piperazine-1-carbonyl)benzyl)-5,6,7,8-tetrahydroquinazoline-2,4(1H,3H)-dione;
1-(4-Fluoro-3-(4-(furan-2-carbonyl)piperazine-1-carbonyl)benzyl)-5,6,7,8-tetrahydroquinazoline-2,4(1H, 3H)-dione;

1-(4-Fluoro-3-(4-(pyrazin-2-yl)piperazine-1-carbonyl) benzyl)-5,6,7,8-tetrahydroquinazoline-2,4(1H,3H)-dione;

1-(4-Fluoro-3-(4-ethylsulfonylpiperazine-1-carbonyl) benzyl)-5,6,7,8-tetrahydroquinazoline-2,4(1H,3H)-dione;

1-(4-Fluoro-3-(4-cyclohexylpiperazine-1-carbonyl)benzyl)-5,6,7,8-tetrahydroquinazoline-2,4(1H,3H)-dione;

1-(4-Fluoro-3-(4-ethylpiperazine-1-carbonyl)benzyl)-5,6,7,8-tetrahydroquinazoline-2,4(1H,3H)-dione;

1-(4-Fluoro-3-(4-(4-fluorobenzoyl)piperazine-1-carbonyl)benzyl)-5,6,7,8-tetrahydroquinazoline-2,4(1H,3H)-dione;

1-(4-Fluoro-3-(4-phenylpiperazine-1-carbonyl)benzyl)-5,6,7,8-tetrahydroquinazoline-2,4(1H,3H)-dione;

1-(4-Fluoro-3-(4-acetylpiperazine-1-carbonyl)benzyl)-5,6,7,8-tetrahydroquinazoline-2,4(1H,3H)-dione;

1-(4-Fluoro-3-(4-(furan-3-carbonyl)piperazine-1-carbonyl)benzyl)-5,6,7,8-tetrahydroquinazoline-2,4(1H,3H)-dione;

1-(4-Fluoro-3-(4-(thiophene-3-carbonyl)piperazine-1-carbonyl)benzyl)-5,6,7,8-tetrahydroquinazoline-2,4(1H,3H)-dione;

1-(4-Fluoro-3-(4-(4-methoxybenzoyl)piperazine-1-carbonyl)benzyl)-5,6,7,8-tetrahydroquinazoline-2,4(1H,3H)-dione;

1-(4-Fluoro-3-(4-(cyclohexylmethyl)piperazine-1-carbonyl)benzyl)-5,6,7,8-tetrahydroquinazoline-2,4(1H,3H)-dione;

1-(4-Fluoro-3-(4-(tetrahydrofuran-2-carbonyl)piperazine-1-carbony)benzyl)-5,6,7,8-tetrahydroquinazoline-2,4(1H,3H)-dione;

1-(6-Fluoro-3-(4-(pyrimidin-2-yl)piperazine-1-carbonyl) benzyl)-5,6,7,8-tetrahydroquinazoline-2,4(1H,3H)-dione;

1-(6-Fluoro-3-(4-(cyclopentylcarbonyl)piperazine-1-carbonyl)benzyl)-5,6,7,8-tetrahydroquinazoline-2,4(1H,3H)-dione;

1-(3-(4-(Pyrimidin-2-yl)piperazine-1-carbonyl)benzyl)-6,7-dihydro-1H-cyclopenta[d]pyrimidine-2,4(3H,5H)-dione;

and pharmaceutically acceptable salts or prodrugs thereof.

The term "alkyl" as employed herein by itself or as part of another group refers to both straight and branched chain radicals of up to ten carbons. Useful alkyl groups include straight-chained or branched $C_{1-10}$ alkyl groups, preferably straight-chained or branched $C_{1-6}$ alkyl groups, more preferably $C_{1-3}$ alkyl groups. Typical $C_{1-10}$ alkyl groups include methyl, ethyl, propyl, isopropyl, butyl, sec-butyl, tert-butyl, 3-pentyl, hexyl and octyl groups.

The term "alkenyl" as employed herein by itself or as part of another group means a straigh or branched chain radical of 2-10 carbon atoms, unless the chain length is limited thereto, including at least one double bond between two of the carbon atoms in the chain. Preferred alkenyl group is $C_{2-4}$ alkenyl. Typical alkenyl groups include ethenyl, 1-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Preferred alkynyl group is $C_{2-4}$ alkynyl. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, preferably $C_{1-6}$ alkyl (that is $C_{1-6}$ alkoxy), more preferably $C_{1-3}$ alkyoxy.

Useful alkylthio groups include sulfur substituted by one of the $C_{1-10}$ alkyl groups mentioned above (preferably $C_{1-6}$ alkyl, more preferably $C_{1-3}$ alkyl), which may be optionally substituted.

Useful amino groups include $-NH_2$, $-NHR_{15}$ and $-NR_{15}R_{16}$, wherein $R_{15}$ and $R_{16}$ are $C_{1-10}$ alkyl or cycloalkyl (such as alkyl or $C_3$-$C_8$ cycloalkyl defined herein); or $R_{15}$ and $R_{16}$ are combined with the N to form a ring structure, such as a piperidine; or $R_{15}$ and $R_{16}$ and N are combined with another group to form a ring, such as a piperazine, which may be optionally substituted.

Generally, the term "optionally substituted" used herein indicates that the group is "optionally subsitutited". The groups as described herein, such as alkyl, alkoxy, alkylthio, alkenyl, alkynyl, cycloalkyl, carbocyclic and heterocyclic groups, may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_6$-$C_{10}$ aryl, $C_3$-$C_8$ cycloalkyl, $C_2$-$C_6$ alkenyl, $C_6$-$C_{10}$ aryl($C_2$-$C_6$)alkenyl, $C_6$-$C_{10}$ aryl($C_2$-$C_6$)alkynyl, saturated and unsaturated heterocyclic group or heteroaryl. In a preferred embodiment, the alkoxy group may be substituted with one or more (e.g., 1 to 4 or 1 to 3 range) substituents, selected from the group of substituents: halo, morpholino, amino including alkylamines, dialkyl amines and carboxyl ester.

Optional substituents on the aryl (including benzoyl and the like), arylalkyl, arylalkenyl, arylalkynyl, heterocyclic group, heteroaryl and heteroarylalkyl groups may be one or more (such as 1, 2, 3, or 4) groups selected from the gourp consisting of halo, methylenedioxy, $C_1$-$C_6$ haloalkyl, $C_6$-$C_{10}$ aryl, $C_3$-$C_8$ cycloalkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$hydroxyalkyl, nitro, amino, amido, ureido, cyano, $C_1$-$C_6$ acylamido, hydroxy, thiol, $C_1$-$C_6$ acyloxy, aminocarbonyl, azido, $C_1$-$C_6$ alkoxy, carboxy, di($C_{1-10}$ alkyl)amido, alkylsulfonyl, aminosulfonyl, dialkylaminosulfonyl, and alkylsulfiniyl.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{6-14}$ aryl groups.

The term "aryialkenyl" is used herein to mean any of the above-mentioned $C_{6-14}$ aryl groups.

The term "arylalkynyl" is used herein to mean any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean alkoxy groups substituted by any of the above-mentioned aryl groups, which may be optionally substituted. Useful arylalkoxy groups include benzyloxy and phenethyloxy.

Useful haloalkyl groups include alkyl groups, such as $C_{1-10}$ alkyl, or preferably $C_{1-6}$ alkyl substituted by one or more fluorine, chlorine, bromine or iodine atoms, e.g., fluorornethyl, difluorornethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups. e.g., benzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle (heterocyclic group) is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), thiazolyl, benzo[b]thienyl, benzo[2,3-b]thienyl, thianthrenyl, furyl (furanyl), pyranyl, isobenzopyranyl, chromenyl, xanthenyl, phenoxanthiinyl, pyrrolyl, imidazolyl, pyrazolyl, pyridyl (pyridlinyl), (including without limitation 2-pyridyl, 3-pyridyl, and 4-pyridyl), pyrazinyl, pyrimidmyl, pyridazinyl, indolizinyl, isoindolyl, 3H-indolyl, indolyl, indazolyl, purinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, tetrahydrocyclopenta[c]pyrazol-3-yl, pyrazolo[1,5-α]pyrimidinyl, 1,2-benzoisoxazoyl-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, tromethane) and N-methylglucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formula I, II or III can be prepared as illustrated by the exemplary reaction in Scheme 1. Reaction of cyclohexanone with diethyl carbonate in THF in the presence of NaH produced ethyl 2-oxocyclohexanecarboxy late. Reaction of ethyl 2-oxocyclohexanecarboxylate with urea at 175-185° C. produced 5,6,7,8-tetrahydroquinazoline-2,4(1H, 3H)-dione. Reaction of 5,6,7,8-tetrahydroquinazoline-2,4(1H, 3H)-dione with hexamethyldisilazane (HMDS) in toluene in the presence of concentrated sulfuric acid, produced the intermediate 2,4-di(trimethylsilyloxy)-5,6,7,8-tetrahydroquinazol. Reaction of 2,4-di(trimethylsilyloxy)-5,6,7,8-tetrahydroquinazoline with methyl 3-(bromomethyl)benzoate in DMF, followed by treatment with 1,4-dioxane and methanol, produced 1-(3-methoxycarbonylbenzyl)-5,6,7,8-tetrahydroquinazoline-2,4(1H,3H)-dione. Treatment of the ester with NaOH in water-methanol produced 1-(3-carboxybenzyl)-5,6,7,8-tetrahydroquinazoline-2,4(1H,3H)-dione. Coupling of the acid with a substituted amine, such as 1-(pyrimidin-2-yl)piperazine, in the presence of coupling agents, such as 2-(7-aza-1H-benzotriazole-1-yl)-1,1,3,3-tetramethyluronium hexafluorophosphate (HATU) and N,N-diisopropylethylamine (DIPEA) in DMF, produced the targeted compound 1-(3-(4-(pyrimidin-2-yl)piperazine-1-carbonyl) benzyl)-5,6,7,8-tetrahydroquinazoline-2,4(1H, 3H)-dione.

Scheme 1

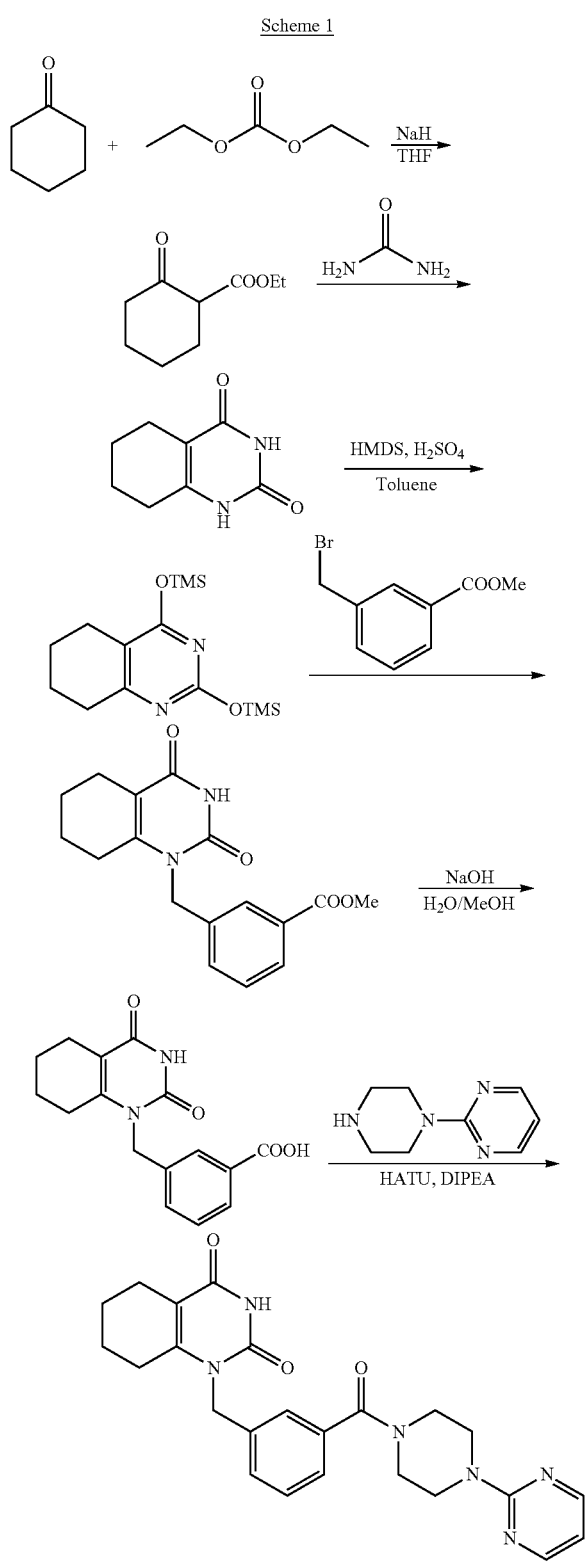

Scheme 2

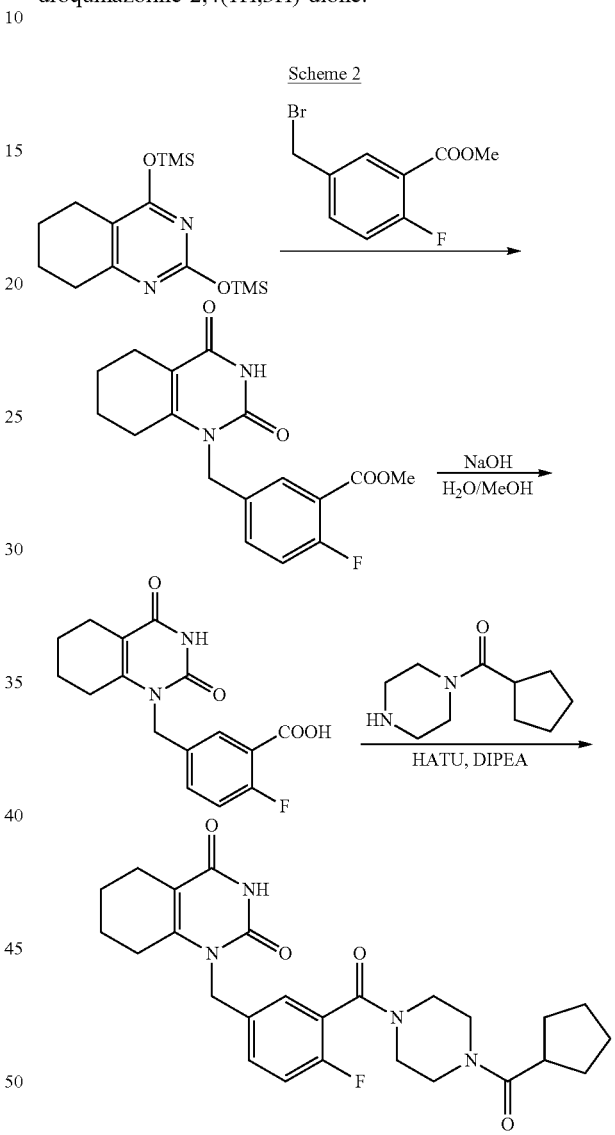

Similarly, compounds of this invention can be prepared as illustrated by the exemplary reaction in Scheme 2. Reaction of the intermediate 2,4-di(trimethylsiloxy)-5,6,7,8-tetrahydroquinazoline with methyl 5-(bromomethyl)-2-fluorobenzoate in DMF, followed by treatment with 1,4-dioxane and methanol, produced 1-(4-fluoro-3-methoxycarbonylbenzyl)-5,6,7,8-tetrahydroquinazol ine-2,4(1H,3H)-dione. Treatment of the ester with NaOH in water-methanol produced 1-(4-fluoro-3-carboxybenzyl)-5,6,7,8-tetrahydroquinazoline-2,4(1H,3H)-dione. Coupling of the acid with a substituted amine, such as 1-cyclopentylcarbonylpiperazine, in the presence of coupling agents, such as HATU and DIPEA in DMF, produced the targeted compound 1-(4-fluoro-3-(4-(cyclopentylcarbonyl)piperazine-1-carbonyl)benzyl)-5,6,7,8-tetrahydroquinazoline-2,4(1H,3H)-dione.

Similarly, compounds of this invention can be prepared as illustrated by the exemplary reaction in Scheme 3. Reaction of cyclopentanone with diethyl carbonate in THF in the presence of NaH produced ethyl 2-oxocyclopentanecarboxylate. Reaction of ethyl 2-oxocyclopentanecarboxylate with urea at 175-185° C. produced 6,7-dihydro-1H-cyclopenta[d]pyrimidine-2,4(3H,5H)-dione. Reaction of 6,7-dihydro-1H-cyclopenta[d]pyrimidine-2,4(3H,5H)-dione with hexamethyldisilazane (HMDS) in toluene in the presence of concentrated sulfuric acid, produced the intermediate 2,4-di(trimethylsilyloxy)-6,7-dihydro-5H-cyclopenta[d]pyrimidine. Reaction of 2,4-di(trimethylsilyloxy)-6,7-dihydro-5H-cyclopenta[d]pyrimidine with methyl 3-(bromomethyl)benzoate in DMF, followed by treatment with 1,4-dioxane and methanol, produced 1-(3-methoxycarbonylbenzyl)-6,7-dihydro-1H-cyclopenta[d]pyrimidine-2,4(3H,5H)-dione. Treatment of the ester with NaOH in water-methanol produced 1-(3-carboxybenzyl)-6,7-dihydro-1H-cyclopenta[d]pyrimidine-2,4(3H,5H)-dione. Coupling of the acid with a substituted amine, such as 1-(pyrimidin-2-yl)piperazine, in the presence of coupling agents, such as HATU and DIPEA in DMF, produced the targeted compound 1-(3-(4-(pyrimidin-2-yl)piperazine-1-carbonyl)benzyl)-6,7-dihydro-1H-cyclopenta[d]pyrimidine-2,4(3H,5H)-dione.

Scheme 3

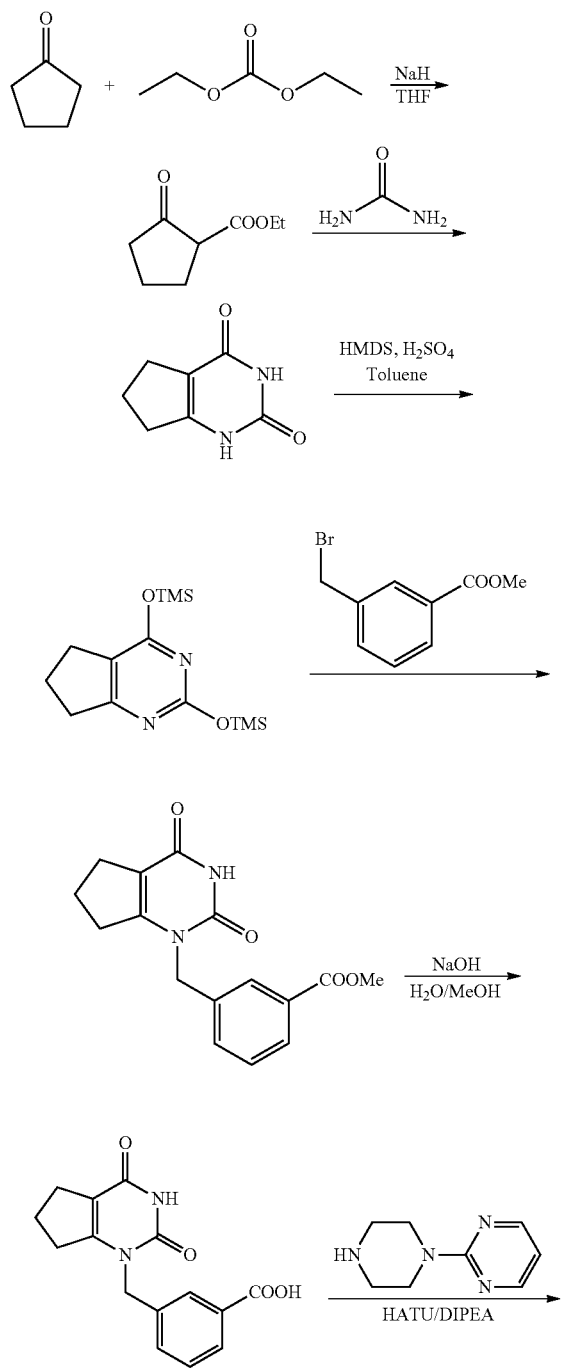

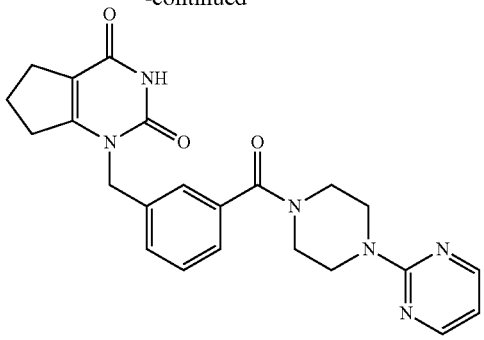

An important aspect of the present invention is the discovery that compounds having Formula I, II or III are PARP inhibitors. Therefore, these compounds are useful for the treatment of a variety of clinical conditions responsive to the inhibition of PARP activity, such as cancer.

The present invention includes a therapeutic method comprising administering to a mammal an effective amount of a compound of Formula I, II or III, or a pharmaceutically acceptable salt or prodrug thereof, wherein said therapeutic method is useful for the treatment of diseases due to abnormal PARP activity (i.e. PARP mediated diseases, furthermore, PARP-1 mediated diseases), such as cancer. Such diseases include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma. choriocarcinoma, mycosis fungoides, head or neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia. cervical hyperplasia, renal cell carcinoma, endometrial carcinoma, polycythemia vera, essential thrombocytosis, adrenal cortex carcinoma, skin cancer, and prostatic carcinoma. Compounds of the present invention, also are useful for the treatment or prevention of other clinical conditions due to abnormal PARP (such as PARP-1) activity, such as excessive cell death, including central nervous system diseases such as stroke and neurodegenerative diseases.

In practicing the therapeutic methods, effective amounts of compositions containing therapeutically effective concentrations of the compounds of Formula I, II or III formulated for oral, intravenous, local or topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate or in some manner reduce, the symptoms associated with the disease. Such amount may be administered as a single dosage or may be administered according to a regimen, whereby it is effective. The amount may cure the disease but, typically, is administered in order to ameliorate the symptoms of the disease.

Typically, repeated administration is required to achieve the desired amelioration of symptom.

The present invention also includes the use of the compounds of Formula I, II or III of the subject invention in the manufacture of a medicament for treating or preventing a disorder responsive to abnormal PARP activity, including cancer. In preferred embodiment, the above-mentioned diseases are selected from cancer. In more preferred embodiment, the above-mentioned diseases are selected from liver cancer, colon cancer, lung cancer and breast cancer. In another preferred embodiment, the above-mentioned drugs may also include other known anti-cancer drugs, but not limited to the various known anti-cancer drugs described herein.

In another embodiment, a pharmaceutical composition comprising a compound of Formula I, II or III or a pharmaceutically acceptable salt thereof, which functions as PARP inhibitor, in combination with a pharmaceutically acceptable vehicle, is provided.

Another embodiment of the present invention is directed to a composition effective to inhibit neoplasia comprising a compound of Formula I, II or III, or a pharmaceutically acceptable salt or prodrug thereof, which functions as a PARP inhibitor, in combination with at least one known anticancer agent or a pharmaceutically acceptable salt thereof. Examples of known anticancer agents which may be used for combination therapy include, but not are limited to DNA damaging anti-cancer drugs, including alkylating agents, such as busulfan, melphalan, chlorambucil, cyclophosphamide, ifosfamide, temozolomide, bendamustine, cis platin, mitomycin C, bleomycin, and carboplatin; topoisomerase I inhibitors, such as camptothecin, irinotecan, and topotecan; topoisomerase II inhibitors, such as doxorubicin, epirubicin, aclarubicin, mitoxantrone, elliptinium and etoposide; RNA/DNA antimetabolites, such as 5-azacytidine, gemcitabine, 5-fluorouracil and methotrexate; DNA antimetabolites, such as 5-fluoro-2'-deoxyuridine, fludarabine, nelarabine, ara-C, alanosine, pralatrexate, pemetrexed, hydroxyurea and thioguanine; antimitotic agents, such as colchicine, vinblastine, vincristine, vinorelbine, paclitaxel, ixabepilone, cabazitaxel, and docetaxel; antibodies, such as campath, Panitumumab, Ofatumumab, Avastin, Herceptin®, Rituxan®; kinase inhibitors such as imatinib, gefitinib, erlotinib, lapatinib, sorafenib, sunitinib, nilotinib, dasatinib, pazopanib, temsirolimus and everolimus; HDAC inhibitors such as vorinostat and romidepsin. Other known anticancer agents which may be used for combination therapy include tamoxifen, letrozole, fulvestrant, mitoguazone, octreotide, retinoic acid, arsenic trioxide, zoledronic acid, bortezomib, thalidomide and lenalidomide.

In practicing the methods of the present invention, the compound of the invention may be administered together with at least one known anticancer agent as part of a unitary pharmaceutical composition. Alternatively, the compound of the invention may be administered apart from at least one known anticancer agent. In one embodiment, the compound of the invention and at least one known anticancer agent are administered substantially simultaneously, i.e. the compounds are administered at the same time or one after the other, so long as the compounds reach therapeutic levels in the blood at the same time. In another embodiment, the compound of the invention and at least one known anticancer agent are administered according to their individual dose schedule, so long as the compounds reach therapeutic levels in the blood.

Another embodiment of the present invention is directed to a composition effective to inhibit neoplasia comprising a bioconjugate of a compound described herein, in bioconjugation with at least one known therapeutically useful antibody, such as Herceptin® or Rituxan®, growth factors, such as DGF, NGF; or cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as Herceptin® or Rituxan®.

Another embodiment of the present invention is directed to a composition effective to inhibit neoplasia comprising a compound of Formula I, II or III, or its pharmaceutically acceptable salt or prodrug, which functions as a PARP inhibitor, in combination with radiation therapy. In this embodiment, the compound of the invention may be administered at the same time as the radiation therapy is administered or at a different time.

Another embodiment of the present invention is directed to a composition effective for post-surgical treatment of cancer, comprising a compound of Formula I, II or III, or its pharmaceutically acceptable salt or prodrug, which functions as a PARP inhibitor. The invention also relates to a method of treating cancer by surgically removing the cancer and then treating the mammal with one of the pharmaceutical compositions described herein.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. If a known anticancer agent is also administered, it is administered in an amount that is effective to achieve its intended purpose. The amounts of such known anticancer agents effective forcancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the invention may he administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present invention with a solution of a pharmaceutically acceptable non-toxic base, such as sodium hydroxide, potassium hydroxide, choline hydroxide, sodium carbonate, Tris, N-methylglucamine and the like.

The pharmaceutical compositions of the invention may be administered to any mammal, which may experience the beneficial effects of the compounds of the invention. Foremost among such mammals are humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearin acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds in water-soluble form, e.g. water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The present invention also includes the use of the compounds of Formula I, II, or III of the subject invention in the manufacture of a medicament for treating or preventing a disorder responsive to the inhibition of PARP activity (especially PARP-1 activity) in a mammal suffering therefrom.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra was recorded at 300 MHz and at 300 K, on a Brücker AMX 300 apparatus. Chemical shifts were recorded as parts per million (ppm) downfield from TMS (0.00 ppm), and J coupling constants were reported in hertz (Hz).

Example 1

Ethyl 2-oxocyclohexanecarboxylate

A 1000 mL flashk was charged with diethyl carbonate (146 mL, 1.2 mol) and 150 mL of dry THF, and NaH (60%, 63 g, 1.6 mol) was added to the mixtrure under stirring. The mixture was heated to reflux for 1 h, and then, a solution of cyclohexanone (50 mL, 0.48 mol) in anhydrous THF (50 mL) was added dropwise to the mixture, and the addition of cyclohexanone was continued for ca. 0.5 h. The mixture was refluxed for an additional 1.5 h. After cooled, the mixture was hydrolyzed by 3N hydrochloric acid, then poured into brine, extracted by DCM (75 mL×3). The combined organic layer was dried and evaporated to give the title compound (66 g, 80% yield) as brown oil which was set to do next step without any purification. MS: m/z 171.3 [M+H]$^+$.

Example 2

5,6,7,8-Tetrahydroquinazoline-2,4(1H,3H)-dione

A mixture of ethyl 2-oxocyclohexanecarboxylate (66 g, 0.39 mol) and urea (68 g, 1.1 mol) was heated at 175-185° C. and stirred for 4-5 h. After cooled to 70° C., adjusted pH=13-14 by NaOH (a.q.), and then the mixture was stirred at 70° C. for 2 h. After cooled to r.t, the mixture was adjusted pH=6-7 by AcOH, and then extracted with DCM for several times. The combined organic layer was dried and evaporated to give the title compound (25 g, 39% yield) as brown solid which was set to do next step without any purification. MS: m/z 167.3 [M+H]$^+$.

Example 3

1-(3-Methoxycarbonylbenzyl)-5,6,7,8-tetrahydroquinazoline ,2,4(1H,3H)-dione

To a mixture of 5,6,7,8-tetrahydroquinazoline-2,4(1H, 3H)-dione (10.4 g, 62 mmol) and hexamethyldisilazane (HMDS, 33 mL, 158 mmol) in toluene (100 mL) was added concentrated sulfuric acid (0.34 mL, 6.2 mmol) at r.t. The mixture was heated to reflux overnight until a clear solution was obtained. After the removal of toluene and excess HMDS with vacuum evaporation, methyl 3-bromomethylbenzoate (16 g, 70 mmol) was added to the residue. The reaction mixture was heated to 115-130° C. and was stirred at this temperature for 4 h. The reaction mixture was diluted with 1,4-dioxane (6 mL) and methanol (100 mL) at 100° C., and was stirred for 30 min. The reaction mixture was evaporated to remove the solvent. The residue was dissolved in ethyl acetate (EA, 300 mL) and washed by 1N hydrochloric acid (100 mL×1) and water (100 mL×3). The organic layer was dried with anhydrous sodium sulfate and evaporated to give the crude product, which was purified by column chromatography on silica gel (petroleum ether: ethyl acetate=2:1) to give the title compound (2.3 g, 12% yield) as yellow powder. $^1$H NMR (DMSO-d$_6$): 11.40 (s, 1H), 7.87 (d, J=7.5 Hz, 1 H), 7.79 (s, 1H), 7.55-7.44 (m, 2H), 5.12 (s, 2H), 3.85 (s, 3H), 2.45-2.35 (m, 2H ), 2.25-2.20 (m, 2H), 1.65-1.40 (m, 4H). MS: m/z 315.4 [M+H]$^+$.

Example 4

1-(3-Carboxybenzyl)-5,6,7,8-tetrahydroquinazoline-2,4(1H,3H)-dione

A solution of 1-(3-methoxycarbonylbenzyl)-5,6,7,8-tetrahydroquinazoline-2,4(1H,3H)-dione (2.3 g, 7.3 mmol) and NaOH (0.59 g, 14.7 mmol) in water-methanol (40 mL and 40 mL) was refluxed for 4 h. After the removal of methanol, the solution was adjusted to pH=2-3 by 3N hydrochloric acid (a.q). The mixture was filtered and the solid was washed by water, and dried to give the title compound (1.8 g, 82% yield) as yellow solid. MS: m/z 301.3 [M+H]$^+$.

Example 5

1-(3-(4-(Pyrimidin-2-yl)piperazine-1-carbonyl)benzyl)-5,6,7,8-tetrahydroquinazoline-2,4(1H, 3H)-dione A mixture of 1-(3-carboxybenzyl)-5,6,7,8-tetrahydroquinazoline-2,4(1H,3H)-dione (0.2 mmol), 1-(pyrimidin-2-yl)piperazine (0.2 mmol), 2-(7-aza-1H-benzotriazole-1-yl)-1,1,3,3-tetramethyluronium hexafluorophosphate (HATU, 0.26 mmol) and N,N-diisopropylethylamine (DIPEA, 0.4 mmol) in DMF (5 mL) was stirred at room temperature overnight. To the mixture was added 50 mL of water and it was extracted with EA (50 mL×3). The organic layer was washed by 1 N hydrochloric acid (50 mL×1) and saturated NaCl aqueous solution (50 mL×1), dried with anhydrous sodium sulfate, and concentrated to give the crude product, which was purified by flash chromatography (DCM: MeOH=20:1) to give the title compound (20.43 mg, 23.3% yield) as white solid. $^1$H NMR (DMSO-d$_6$): 11.35 (s, 1H), 8.39 (d, J=4.5 Hz, 2H), 7.48-7.41 (m, 1H), 7.36-7.24 (m, 3H), 6.67 (t, J=4.8 Hz, 1H), 5.10 (s, 2H), 3.88-3.20 (m, 8H), 2.46-2.42 (m, 2H), 2.25-2.21 (m, 2H), 1.69-1.43 (m, 4H). MS: m/z 447.4 [M+H]$^+$.

The following compounds were prepared from 1-(3-carboxybenzyl)-5,6,7,8-tetrahydroquinazoline-2,4(1H,3H)-dione and the corresponding substituted piperazine using a procedure similar to those described for the synthesis of compound of Example 5.

Example 6

1-(3-(4-(Cyclopropylcarbonyl)piperazine-1-carbonyl)benzyl)-5,6,7,8-tetrahydroquinazoline-2, 4(1H, 3H)-dione $^1$H NMR(DMSO-d$_6$): 11.37 (s, 1H), 7.45 (t, J=7.7 Hz, 1H), 7.35-7.23 (m, 3H), 5.09 (s, 2H), 3.78-3.42 (m, 8H), 2.46-2.42 (m, 2H), 2.25-2.22 (m, 2H), 1.99-1.95 (m,1H), 1.63-1.52 (m, 4H), 0.74-0.71 (m, 4H). MS: m/z 437.3 [M+H]$^+$.

Example 7

1-(3-(4-(Thiophene-2-carbonyl)piperazine-1-carbonyl)benzyl)-5,6,7,8-tetrahydroquinazoline-2,4(1H, 3H)-dione $^1$H NMR (DMSO-1$_6$): 11.37 (s, 1H), 7.78 (d, J=3.9 Hz, 1H), 7.60-7.00 (m, 6H), 5.10 (s, 2H), 3.90-3.20 (m, 8H), 2.46-2.42 (m, 2H), 2.30-2.22 (m, 2H), 1.70-1.40 (m, 4H). MS: m/z 479.2 [M+H]+.

Example 8

1-(3-(4-(Thiazol-2yl)piperazine-1carbonyl)benzyl)-5,6,7,8-tetrahydroquinazoline-2,4(1H,3H)-dione $^1$H NMR (DMSO-d$_6$): 11.37 (s, 1H), 7.45 (t, J=7.5 Hz, 1H), 7.34 (d, J=7.8 Hz, 1H), 7.30-7.21 (m, 2H), 7.19 (d, J=3.6 Hz, 1H), 6.89 (d, J=3.6 Hz, 1H), 5.04 (s, 2H), 3.80-3.50 (m, 8H), 2.45-2.42 (m, 2H), 2,28-2.23 (m, 2H), 1.70-1.40 (m, 4H). MS: m/z 452.2 [M +H]$^+$.

Example 9

1-(3-(4-(Cyclopentylcarbonyl)piperazine-1-carbonyl)benzyl)-5,6,7,8-tetrahydroquinazoline-2, 4(1H, 3H)-dione $^1$H NMR (DMSO-d$_6$): 11.37 (s, 1H), 7.44 (t, J=7.7 Hz, 1H), 7.35-7.20 (m, 3H), 5.09 (s, 2H), 3.70-3.40 (m, 8H), 3.00-2.90 (m, 1H), 2.45-2.41 (m, 2H), 2.26-2.22 (m, 2H), 1.80-1.40 (m, 12H). MS: m/z 465.3 [M+H]$^+$.

Example 10

1-(3-(4-Benzoylpiperazine-1-carbonyl)benzyl)-5,6,7,8-tetrahydroquinazoline-2,4(1H,3H)-dione $^1$H NMR (DMSO-d$_6$): 11.36 (s, 1H), 7.46-7.40 (m, 6H), 7.33-7.22 (m, 3H), 5.09 (s, 2H), 3.80-3.40 (m, 8H), 2.46-2.35 (m, 2H), 2.24-2.18 (m, 2H), 1.65-1.45 (m. 4H). MS: m/z 473.3 [M+H]$^+$.

Example 11

1-(3-(4-(Pyridin-2-yl)piperazine-1-carbonyl)benzyl)-5,6,7,8-tetrahydroquinazoline-2,4(1H,3H)-dione $^1$H NMR (DMSO-d$_6$): 11.37 (s, 1H), 8.12 (dd, J=4.8 and 1.2 Hz, 1H), 7.56 (t, J=7.8 Hz, 1H), 7.45 (t, J=7.5 Hz, 1H), 7.34 (d, J=7.8 Hz, 1H), 7.30-7.20 (m, 2H), 6.83 (d, J=8.7 Hz, 1H), 6.67 (t, J=6.0 Hz, 1H), 5.10 (s, 2H), 3.85-3.40 (m, 8H), 2.46-2.41 (m, 2H), 2.25-2.21 (m, 2H), 1.75-1.45 (m, 4H). MS: m/z 446.3 [M+H]$^+$.

Example 12

1-(3-(4-(Cyclohexylcarbonyl)piperazine-1-carbonyl)benzyl)-5,6,7,8-tetrahydroquinazoline-2,4(1H, 3H)-dione $^1$HNMR(DMSO-d$_6$): 11.35 (s, 1H), 7.42 (t, J=7.7 Hz, 1H), 7.31-7.24 (m, 2H), 7.20 (s, 1H), 5.07 (s, 2H), 3.62-3.46 (m, 8H), 2.62-2.56 (m, 1H), 2.42-2.38 (m, 2H), 2.23-2.19 (m, 2H), 1.70-1.52 (m, 9H), 1.38-1.13 (m, 5H). MS: m/z 479.30 [M+H]$^+$.

Example 13

1-(3-(4-(Furan-2-carbonyl)piperazine-1-carbonyl)benzyl)-5,6,7,8-tetrahydroquinazoline-2,4(1H, 3H)-dione 1H NMR(DMSO-d6): 11.35 (s, 1H), 7.82 (d, J=0.9 Hz, 1H), 7.43 (t, J=7.5 Hz, 1H), 7.32 (d, J=7.5 Hz, 1H), 7.26-7.22 (m, 2H), 7.00 (d, J=3.3 Hz, 1H), 6.61 (dd, J=3.3 and 1.8 Hz, 1H), 5.08 (s, 2H), 3.67-3.44 (m, 8H), 2.42-2.38 (m, 2H), 2.22-2.18 (m, 2H), 1.62-1.51 (m, 4H). MS: m/z 463.3 [M+H]$^+$.

Example 14

1-(3-(4-(Cyclobutylcarbonyl)piperazine-1-carbonyl)benzyl)-5,6,7,8-tetrahydroquinazoline-2,4(1H,3H)-dione $^1$H NMR (DMSO-d$_6$): 11.37 (s, 1H), 7.44 (t, J=7.5 Hz, 1H), 7.32-7.25 (m, 2H), 7.21 (s, 1H), 5.09 (s, 2H), 3.70-3.10 (m, 9H), 2.46-2.37 (m, 2H), 2.30-2.02 (m, 6H), 2.00-1.40 (m, 6H). MS: m/z 451.3 [M+H]$^+$.

Example 15

1-(3-(4-(Thiophene-3-carbonyl)piperazine-1-carbony)benzyl)-5,6,7,8-tetrahydroquinazoline-2,4(1H, 3H)-dione $^1$H NMR (DMSO-d$_6$): 11.37 (s, 1H), 7.81 (s, 1H), 7.70-7.55 (m, 1H), 7.50-7.39 (m, 1H), 7.34-7.23 (m, 4H), 5.09 (s, 2H), 3.80-3.20 (m, 8H), 2.43-2.39 (m, 2H), 2.24-2.20 (m, 2H), 1.70-1.40 (m, 4H). MS: m/z 479.2 [M+H]$^+$.

Example 16

1-(3-(4-(Pyrazin-2-yl)piperazine-1-carbonyl)benzyl)-5,6,7,8-tetrahydroquinazoline-2,4(1H,3H)-dione $^1$H NMR (DMSO-d$_6$): 11.37 (s, 1H), 8.33 (s, 1H), 8.10 (s, 1H), 7.87 (d, J=2.7 Hz, 1H), 7.46 (t, J=7.5 Hz, 1H), 7.35 (d, J=7.8 Hz, 1H), 7.31-7.23 (m, 2H), 5.10 (s, 2H), 3.80-3.40 (m, 8H), 2.47-2.37 (m, 2H), 2.27-2.17 (m, 2H), 1.70-1.45 (m, 4H). MS: m/z 447.3 [M+H]$^+$.

The compound of Example 17 was prepared from 5,6,7,8-tetrahydroquinazoline-2,4(1H,3H)-dione and methyl 5-bromomethylbenzoate using a procedure similar to those described for the synthesis of compounds of Example 3 and 4.

Example 17

1-(4-Fluoro-3-carboxybenzyl)-5,6,7,8-tetrahydroquinazoline-2,4(1H,3H)-dione (a) 1-(4-Fluoro-3-methoxycarbonylbenzyl)-5,6,7,8-tetrahydroquinazoline-2,4(1H,3H)-dione.

$^1$H NMR (DMSO-d$_6$): 11.40 (s, 1H), 7.73 (dd, J=6.9 and 2.4 Hz, 1H), 7.50-7.45 (m, 1H), 7.35-7.30 (m, 1H), 5.07 (s, 2H), 3.85 (s, 3H), 2.45-2.35 (m, 2H), 2.25-2.15 (m, 2H), 1.65-1.45 (m, 4H). MS: m/z 333.2 [M+H]$^+$. (b) 1-(4-Fluoro-3-carboxybenzyl)-5,6,7,8-tetrahydroquinazoline-2,4(1H, 3H)-dione. MS: m/z 319.2 [M+H]$^+$.

The following compounds were prepared from 1-(4-fluoro-3-carboxybenzyl)-5,6,7,8-tetrahydroquinazoline-2,4 (1H,3H)-dione and the corresponding substituted piperazine using a procedure similar to those described for the synthesis of compound of Example 5.

Example 18

1-(4-Fluoro-3-(4-benzoylpiperazine-1-carbonyl)benzyl)-5,6,7,8-tetrahydroquinazoline-2,4(1H,3H)-dione $^1$H NMR (DMSO-d$_6$): 11.36 (s, 1H), 7.49-7.38 (m, 5H), 7.33-7.22 (m, 3H), 5.05 (s, 2H), 3.75-3.45 (m, 8H), 2.43-2.38 (m, 2H), 2.23-2.19 (m, 2H), 1.65-1.45 (m4H) MS: m/z 491.3 [M+H]$^+$.

Example 19

1-(4-Fluoro-3-(4-(cyclopropylcarbonyl)piperazine-1-carbonyl)benzyl)-5,6,7,8-tetrahydroquinazoline-2,4 (1H, 3H)-dione $^1$H NMR(DMSO-d$_6$): 11.37 (s, 1H), 7.32-7.29 (m, 3H), 5.05 (s, 2H), 3.64-3.16 (m, 8H), 2.43-2.39 (m, 2H), 2.24-2.20 (m, 2H), 2.03-1.89 (m, 1H), 1.63-1.53 (m, 4H), 0.75-0.71 (m, 4H). MS: m/z 455.3 [M+H]$^+$.

Example 20

1-(4Fluoro-3-(4-(pyrimidin-2-yl)piperazine-1-carbonylbenzyl)-5,6,7,8-tetrahydroquinazoline -2,4(1H, 3H)-dione $^1$H NMR (DMSO-d$_6$): 11.37 (s, 1H), 8.39 (d, J=4.5 Hz, 2H), 7.40-7.25 (m, 3H), 6.68 (t, J=4.8 Hz, 1H), 5.06 (s, 2H), 3.83-3.20 (m, 8H), 2.45-2.40 (m, 2H), 2.25-2.20 (m, 2H), 1.70-1.45 (m, 4H). MS: m/z 465.3 [M+H]$^+$.

Example 21

1-(4-Fluoro-3-(4-(thiophene-2-carbonyl)piperazine-1-carbonyl)benzyl)-5,6,7,8-tetrahydroquinazoline-2, 4(1H, 3H)-dione $^1$H NMR (DMSO-d$_6$): 11.35 (s, 1H), 7.76 (d, J=4.8Hz, 1H), 7.42 (d, J=3.3 Hz, 1H), 7.35-7.20 (m, 3H), 7.11 (dd, J=4.8 and 3.9 Hz, 1H), 5.04 (s, 2H), 3.80-3.20 (m, 8H), 2.44-2.36 (m, 2H), 2.24-2.16 (m, 2H), 1.70-1.40 (m, 4H). MS: m/z 497.3 [M+H]$^+$.

Example 22

1-(4-Fluoro-3-(4-(cyclobutylcarbonyl)piperazine-1-carbonyl)benzyl)-5,6,7,8-tetrahydroquinazoline-2,4 (1H, 3H)-dione $^1$H NMR (DMSO-d$_6$): 11.37 (s, 1H), 7.40-7.20 (m, 3H), 5.05 (s, 2H), 3.70-3.10 (m, 9H), 2.43-2.39 (m, 2H), 2.24-2.10 (m, 6H), 2.00-1.40 (m, 6H). MS: m/z 469.3 [M+H]$^+$.

Example 23

1-(4-Fluoro-3-(4-(thiazol-2-yl)piperazine-1-carbonyl)benzyl)-5,6,7,8-tetrahydroquinazoline-2, 491H, 3H)-dione $^1$H NMR (DMSO-d$_6$): 11.36 (s, 1H), 7.50-7.23 (m, 3H), 7.19 (d, J=3.3 Hz, 1H), 6.89 (d, J=3.6 Hz, 1H), 5.06 (s, 2H), 3.90-3.20 (m, 8H), 2.46-2.41 (m, 2H), 2.26-2.21 (m, 2H), 1.70-1.40 (m, 4H). MS: m/z 470.2 [M+H]$^+$.

Example 24

1-(4-Fluoro-3-(4-(cyclohexylcarbonyl)piperazine-1-carbonyl)benzyl)-5,6,7,8-tetrahydroquinazoline-2,4 (1H, 3H)-dione $^1$H NMR(DMSO-d$_6$): 11.37 (s, 1H), 7.31-7.29 (m, 3H), 5.05 (s, 2H), 3.58-3.18 (m, 8H), 2.51-2.49 (m, 1H), 2.44-2.40 (m, 2H), 2.24-2.20 (m, 2H), 1.69-1.24 (m, 14H). MS: m/z 497.3 [M+H]$^+$.

Example 25

1-(4-Fluoro-3-(4-(cyclopentylcarbonyl)piperazine-1-carbonyl)benzyl)-5,6,7,8-tetrahydroquinazoline-2,4 (1H, 3H)-dione $^1$H NMR (DMSO-d$_6$): 11.36 (s, 1H), 7.34-7.22 (m, 3H), 5.05 (s, 2H), 3.70-3.35 (m, 8H), 3.00-2.90 (m, 1H), 2.45-2.41 (m, 2H), 2.24-2.20 (m, 2H), 1.80-1.40 (m, 12H). MS: m/z 483.3 [M+H]$^+$.

Example 26

1-(4-Fluoro-3-(4-(pyridin-2-yl)piperazine-1-carbonyl)benzyl)-5.6,7,8-tetrahydroquinazoline-2 ,4(1H, 3H)-dione $^1$H NMR (DMSO-d$_6$): 11.37 (s. 1H), 8.13 (dd, J=4.8 and 1.2 Hz, 1H), 7.56 (t, J=7.8 Hz, 1H), 7.34-7.25 (m, 3H), 6.84 (d, J=-8.4 Hz, 1H), 6.71-6.65 (m, 1H), 5.06 (s, 2H), 3.80-3.40 (m, 8H), 2.47-2.42 (m, 2H), 2.26-2.21 (m, 2H), 1.70-1.45 (m, 4H). MS: m/z 464.2 [M+H]$^+$.

Example 27

1-(4-Fluoro-3-(4-(furan-2-carbonyl)piperazine-1-carbonyl)benzyl)-5,6,7,8-tetrahydroquinazoline-2,4 (1H, 3H)-dione $^1$H NMR (DMSO-d$_6$):11.37 (s, 1H), 7.84 (d, J=0.9 Hz, 1H), 7.32-7.28 (m, 3H), 7.03 (d, J=2.7 Hz, 1H), 6.63 (dd, J=3.6 and 1.8 Hz, 1H), 5.06 (s. 2H), 3.80-3.20 (m, 8H), 2.46-2.41 (m, 2H), 2.25-2.21 (m, 2H), 1.63-1.35 (m, 4H). MS: m/z 481.3 [M+H]$^+$.

Example 28

1-(4-Fluoro-3-(4-(pyrazin-2-yl)piperazine-1-carbonyl)benzyl)-5,6,7,8-tetrahydroquinazoline-2,4(1H, 3H)-dione $^1$H NMR (DMSO-d$_6$): 11.36 (s, 1H), 8.33 (s, 1H), 8.12-8.08 (m, 1H), 6.68 (d, J=2.7 Hz, 1H), 7.35-7.25 (m, 3H), 5.06 (s, 2H), 3.85-3.45 (m, 8H), 2.47-2.41 (m, 2H), 2.26-2.20 (m, 2H), 1.75-1.45 (m, 4H). MS: m/z 465.3 [M+H]$^+$.

Example 29

1-(4-Fluoro-3 1-(4-ethylsulfonylpiperazine-1-carbonyl)benzyl)-5,6,7,8-tetrahydroquinazoline-2,4(1H, 3H)-dione $^1$H NMR (DMSO-d6): 11.36 (s, 1H), 7.40-7.20 (m, 3H), 5.05 (s, 2H), 3.80-3.10 (m, 8H), 3.07 (q, J=7.4 Hz, 2H), 2.44-2.38 (m, 2H), 2.25-2.20 (m, 2H), 1.70-1.40 (m, 4H), 1.21 (t, J=7.4 Hz, 3H). MS: m/z 479.2 [M+H]$^+$.

Example 30

1-(4-Fluoro-3-(4-cyclohexylpiperazine-1-carbonyl) benzyl)-5,6,7,8-tetrahydroquinazoline-2,4(1H, 3H)-dione $^1$H NMR (DMSO-d$_6$): 11.37 (s, 1H), 7.40-7.25 (m, 2H), 7.21-7.10 (m, 1H), 5.05 (s, 2H), 3.70-3.50 (m, 2H), 3.25-3.10 (m, 2H), 2.70-2.10 (m, 9H). 1.80-1.00 (m, 14H). MS: m/z 469.3 [M+H]$^+$.

Example 31

1-(4-Fluoro-3-(4-ethylpiperazine-1-carbonyl)benzyl)-5,6,7,8-tetrahydroquinazoline-2,4(1H, 3H)-dione $^1$H NMR (DMSO): 11.39 (s, 1H), 7.29-7.27 (m, 2H), 7.20-7.18 (m, 1H), 5.04 (s, 2H), 3.62-3.10 (m, 8H), 2.42-2.20 (m, 6H), 1.62-1.53 (m, 4H), 0.99 (t, J=7.2 Hz, 3H). MS: m/z 415.3 [M+H]$^+$.

Example 32

1-(4-Fluoro-3-(4-(4-fluorobenzoyl)piperazine-1-carbonyl)benzyl)-5,6,7,8-tetrahydroquinazoline-2,4(1H, 3)-dione $^1$H NMR (DMSO-d$_6$): 11.36 (s, 1H), 7.52-7.48 (m, 2H), 7.31-7.25 (in, 5H), 5.05 (s, 2H), 3.80-3.20 (m, 8H), 2.44-2.38 (m, 2H), 2.25-2.20 (m, 2H), 1.70-1.40 (m, 4H). MS: m/z 509.3 [M+H]$^+$.

Example 33

1-(4-Fluoro-3-(4-phenylpiperazine-1-carbonyl)benzyl)-5,6,7,8-tetrahydroquinazoline-2,4(1H, 3H)-dione $^1$H NMR (DMSO): 11.36 (s, 1H), 7.32-7.20 (m, 5H), 6.94 (d, J=7.8 Hz, 2H), 6.82 (t, J=7.8 Hz, 1H), 5.06 (s, 2H), 3.80-3.00 (m, 8H), 2.48-2.40 (m, 2H), 2.24-2.20 (m, 2H), 1.63-1.53 (m, 4H). MS: m/z 463.3 [M=H]$^+$.

Example 34

1-(4-Fluoro-3-(4-acetylpiperazine-1-carbonyl)benzyl)-5,6,7,8-tetrahydroquinazoline-2,4(1H,3 H)-dione $^1$H NMR (DMSO-d$_6$): 11.36 (s, 1), 7.40-7.20 (m, 3H), 5.05 (s, 2H), 3.70-3.10 (m, 8H), 2.45-2.41 (m, 2H), 2.25-2.20 (m, 2H), 2.01 (d, J=15 Hz, 3H), 1.61-1.23 (m, 4H). MS: m/z 429.2 [M+H]$^+$.

Example 35

1-(4-Fluoro-3-(4-(furan-3-carbonyl)piperazine-1-carbonyl)benzyl)-5,6,7,8-tetrahydroquinazoline-2,4(1H, 3H)-dione $^1$H NMR (DMSO-d$_6$): 11.37 (s, 1H) 8.06 (s, 1H), 7.74 (s, 1H), 7.40-7.20 (in, 3H), 6.75-6.60 (m, 1H), 5.05 (s, 2H), 3.80-3.20 (m, 8H), 2.50-2.35 (m, 2H), 2.30-2.10 (m, 2H), 1.70-1.40 (m, 4H). MS: m/z 481.2 [M+H]$^+$.

Example 36

1-(4-Fluoro-3-(4-(thiophene-3-carbonyl)piperazine-1-carbonyl)benzyl)-5,6,7,8-tetrahydroquinazoline-2,4(1H, 3H)-dione $^1$H NMR (DMSO-d$_6$): 11.36 (s, 1H), 7.82 (s, 1H), 7.70-7.55 (m, 1H), 7.40-7.15 (m, 4H), 5.05 (s, 2H), 3.80-3.20 (m, 8H), 2.50-2.35 (m, 2H), 2.30-2.10 (m, 2H), 1.70-1.40 (m, 4H). MS: m/z 497.2 [M+H]$^+$.

Example 37

1-(4-Fluoro-3-(4-(4-methoxybenzoyl)piperazine-1-carbonyl)benzyl)-5,6,7,8-tetrahydroquinazoline-2,4(1H, 3H)-dione $^1$H NMR (DMSO-d$_6$): 11.37 (s, 1H), 7.39 (d, J=8.4 Hz, 2H), 7.38-7.20 (m, 3H), 6.98 (d, J=8.4 Hz, 2H), 5.05 (s, 2H), 3.79 (s, 3H), 3.75-3.20(m, 8H), 2.43-2.39 (m, 2H), 2.24-2.20 (m, 2H), 1.70-1.40 (m, 4H). MS: m/z 521.3 [M+H]$^+$.

Example 38

1-(4-Fluoro-3-(4-(cyclohexylmethyl)piperazine-1-carbonyl)benzyl)-5,6,7,8-tetrahydroquinazoline-2,4(1H, 3H)-dione $^1$H NMR (DMSO-d$_6$): 11.37 (s, 1H), 7.35-7.10 (m, 3H), 5.04 (s, 2H), 3.70-3.50 (m, 2H), 3.25-3.10 (m, 2H), 2.50-2.35 (m, 4H), 2.30-2.15 (m, 4H), 2.08 (d, JH=7.2 Hz, 2H), 1.80-0.70 (m, 15H). MS: m/z 483.3 [M+H]$^+$.

Example 39

1-(4-Fluoro-3-(4-(tetrahydrofuran-2-carbonyl)piperazine-1-carbonyl)benzyl)-5,6,7,8-tetrahydroquinazoline-2,4(1H, 3H)-dione $^1$H NMR (DMSO-d$_6$): 11.36 (s, 1H), 7.40-7.20 (m, 3H), 5.05 (s, 2H), 4.80-4.55 (m, 1H), 3.85-3.35 (m, 8H), 3.30-3.10 (m, 2H), 2.50-2.32 (m, 2H), 2.30-2.12 (m, 2H), 2.10-1.70 (m, 4H), 1.61-1.54 (m, 4H). MS: m/z 485.3 [M+H]$^+$.

Compounds of Example 40 were prepared from 5,6,7,8-tetrahydroquinazoline-2,4(1H, 3H)-dione and methyl 3-(bromomethyl)-4-fluorobenzoate using a procedure similar to those described for the synthesis of compounds of Example 3 and 4.

Example 40

1-(6-Fluoro-3-carboxybenzyl)-5,6,7,8-tetrahydroquinazoline-2,4(1H, 3H)-dione (a) 1-(6-Fluoro-3-methoxycarbonylbenzyl)-5,6,7,8-tetrahydroquinazoline-2,4(1H ,31H)-dione. MS: m/z 333.2 [M+H]$^+$. (b) 1-(6-Fluoro-3-carboxybenzyl)-5,6,7,8-tetrahydroquinazoline-2,4(1H,3H)-dione. MS: m/z 319.1 [M+H]$^+$.

The following compounds were prepared from 1-(6-fluoro-3-carboxybenzyl)-5,6,7,8-tetrahydroquinazoline-2,4 (1H, 3H)-dione and the corresponding substituted piperazine using a procedure similar to those described for the synthesis of compound of Example 5.

Example 41

1-(6-Fluoro-3-(4-(pyrimidin-2-yl)piperazine-1l-carbonylbenzyl)-5,6,7,8-tetrahydroquinazoline-2,4(1H, 3H)-dione $^1$H NMR (DMSO-d6): 11.36 (s, 1H), 8.36 (d, J=4.8 Hz, 2H), 7.45-7.38 (m, 1H), 7.35-7.25 (m, 1H), 7.11 (d, J=6.0 Hz, 1H), 6.65 (t, J=4.8 Hz, 1H), 5.08 (s, 2H), 3.95-3.20 (m, 8H). 2.47-2.41 (m, 2H), 2.25-2.20 (m, 2H), 1.70-1.45 (m, 4H). MS: m/z 465.2 [M+H]$^+$.

Example 42

1-(6-Fluoro-3-(4-(cyclopentylcarbonyl)piperazine-1-carbonyl)benzyl)-5,6,7,8-tetrahydroquinazoline-2.4 (1H, 3H)-dione $^1$H NMR (DMSO-d$_6$): 11.37 (s, 1H), 7.43-7.36 (m, 1H), 7.35-7.25 (m, 1H), 7.09 (dd, J=4.2 and 1.8 Hz, 1H), 5.07 (s, 2H), 3.80-3.20 (m, 8H), 3.80-2.90 (m, 1H), 2.45-2.41 (m, 2H), 2.26-2.21 (m, 2H), 1.80-1.40 (m, 12H). MS: m/z 483.3 [M+H]$^+$.

Compounds of Example 43 were prepared from cyclopentanone, diethyl carbonate and urea using a procedure similar to those described for the synthesis of compounds of Example 1 and example 2.

Example 43

6,7-Dihydro-1H-cyclopenta[d]pyrimidine-2,4(3H, 5H)-dione (a) 2-Ethoxycarbonylcyclopentanone. MS: m/z 157.3 [M+H]$^+$. (b) 6,7-Dihydro-1H-pentanone[d]pyrimidine-2,4 (3H, 5H)-dione. MS: m/z 153.2 [M+H]$^+$.

Compounds of Example 44 were prepared from 6,7-dihydro-1H-cyclopenta[d]pyrimidine-2,4(3H,5H)-dione and methyl 3-(bromomethyl)benzoate using a procedure similar to those described for the synthesis of compounds of Example 3 and 4.

Example 44

1-(3-Carboxybenzyl)-6,7-dihydro-1H-cyclopenta[d]pyrimidine-2,4(3H, 5H)-dione (a) 1-(3-Methoxycarbonylbenzyl)-6,7-dihydro-1H-cyclopenta[d]pyrimidine-2,4(3H,5H)-dione. MS: m/z 301.3 [M+H]$^+$. (b) 1-(3-Carboxybenzyl)-6,7-dihydro-1H-cyclopenta[d]pyrimidine-2,4(3H, 5H)-dione. MS: m/z 287.3 [M+H]$^+$.

The following compounds were prepared from 1-(3-carboxybenzyl)-6,7-dihydro-1H-cyclopenta[d]pyrimidine-2,4 (3H, 5H)-dione and the corresponding substituted piperazine using a procedure similar to those described for the synthesis of compound of Example 5.

Example 45

1-(3-(4-(Pyrimidin-2-yl)piperazine-1-carbonylbenzyl)-6,7-dihydro-1H-cyclopenta[d]pyrimidine-2,4 (3H, 5H)-dione $^1$H NMR (DMSO-d$_6$): 11.20 (s, 1H), 8.38 (d, J=4.5 Hz, 2H), 7.48-7.43 (m, 1H), 7.38-7.31 (m, 3H), 6.67 (t, J=4.8 Hz, 1H), 4.98 (s, 2H), 3.90-3.20 (m, 8H), 2.85-2.70 (m, 2H), 2.60-2.45 (m, 2H), 2.05-1.85 (m, 2H). MS: m/z 433.4 [M+H]$^+$.

Example 46

Evaluation of the synergistic potentiation effects of 1-(3-(4-(pyrimidin-2-yl)piperazine-1-carbonyl)benzyl)-5,6,7,8-tetrahydroquinazoline-2,4(1H,3H)-dione and analogs on the growth inhibiting activity of MMS using a MTT based cell viability assay The synergistic potentiation effect of PARP inhibitors on the growth inhibiting activity of DNA damaging anticancer drugs such as methyl methanesulphonate (MMS) were measured with SW620 human colorectal cancer cells (Shanghai Cancer Institute) using a MTT based cell viability assay. SW620 cells were grown and maintained in RPMI1640 (Gibco) medium supplemented with 10% FBS (Hyclone). In the first day of experiment, 4000 cells were seeded to each well of a 96-well cell culture plate and incubated at 37° C. and 5% $CO_2$ in a cell culture incubator overnight. In the next day, the cell culture medium was removed. 180 µl fresh medium containing 1.5 µg/ml MMS and 20 µl of 10-fold concentration of testing compounds or reference compounds (AZD2281) were added to each well sequencially. The serial dilutions of the reference compounds and the compounds to be tested were made with a 1:3 and 1:10 fashion in DMSO. The 10-fold concentrated solutions of these compounds were made by mixing 10 µl of the serial dilutions in DMSO with 90 µl fresh medium. The final concentration of DMSO in the medium was 1%. The cells were incubated at 37° C. in 5% $CO_2$ cell culture incubator for additional 5 days (120 hours). Afterwards, the 96-well cell culture plate was taken out and 20 µl of MTT solution was added to each well and incubated at 37° C. for 4 h. The medium was removed and 100 µl DMSO was added to each well. The 96—well cell culture plates were shaked adequately for 10 min and readed in a Varioskan Flash plate reader (Thermo Fisher Scientific) at 520 and 690 nm. The data were analyzed by Prism 5 software (GraphPad). The obtained 520 nm absorbance readings substracting corresponding 690 nm reading were analyzed and plotted against the Log scale of the compound concentrations. The curves were fitted using the following equation to calculate the $IC_{50}$ value of each compound, Y (absorbance)=minimal absorbance value+(maximal absorbance value—minimal absorbance value)/(1+10^(LogC−LogIC$_{50}$)), C was the compound concentration. The calculated $IC_{50}$ values can be used to describe the synergistic potentiation effects of a specific compound on the growth inhibiting activity of MMS, which are listed in table 1.

TABLE 1

Compounds potentiate the growth inhibiting activity of MMS ($IC_{50}$)

| Example | 5 | 6 | 7 | 8 | 9 | 10 | 11 | 12 |
|---|---|---|---|---|---|---|---|---|
| $IC_{50}$ (nM) | 15 | 120 | 21 | 11 | 12 | 36 | 6.9 | 9.7 |
| Example | 13 | 14 | 15 | 16 | 18 | 19 | 20 | 21 |
| $IC_{50}$ (nM) | 33 | 22 | 31 | 13 | 9.5 | 25 | 0.83 | 1.3 |
| Example | 22 | 23 | 24 | 25 | 26 | 27 | 28 | 29 |
| $IC_{50}$ (nM) | 1.7 | 1.5 | 3.6 | 1.9 | 2.3 | 9.7 | 4.9 | 18 |
| Example | 30 | 31 | 32 | 33 | 34 | 35 | 36 | 37 |

TABLE 1-continued

| Compounds potentiate the growth inhibiting activity of MMS ($IC_{50}$) | | | | | | | |
|---|---|---|---|---|---|---|---|
| $IC_{50}$ (nM) | 12 | 31 | 6.3 | 7.6 | 42 | 4.0 | 3.4 | 14 |
| Example | 38 | 39 | 41 | 42 | 45 | AZD2281 | |
| $IC_{50}$ (nM) | 10 | 15 | 4.1 | 4.8 | 138 | 46 | |

Therefore, as measured 1-(3-(4-(pyrimidin-2-yl)piperazine-1-carbonyl)benzyl)-5,6,7,8-tetrahydroquinazoline-2,4 (1H, 3H)-dione (Example 5) and analogs have excellent potentiation effects on the growth, inhibiting activity of DNA damaging anticancer agent, such as MMS. Compounds of Example 5, 20 and 23 were found to be 3-40 folds more active than the reference compound AZD2281.

Example 47

Determination of the synergistic potentiation effect of 1-(3-(4-(pyrimidin-2-yl)piperazine-1-carbonyl)benzyl)-5,6,7,8-tetrahydroquinazoline-2,4(1H, 3H)-dione and analogs on MMS induced apoptosis using a cell based caspase-3 activity assay Human breast cancer cell line T47D (Nanjing KeyGEN Biotech. CO., LTD.) was used to determine the potentiation effect of PARP-1 inhibitors on the apoptosis inducing activity of DNA damaging anticancer drugs such as MMS. Intracellular caspase-3 activity was used to measure cell apoptosis. Briefly, T47D cells were grown in DMEM/F12 cell culture medium (Hyclone) supplemented with 0.2 µ/ml insulin (Genview) and 10% FBS (Hyclone). A day before experiment, 20000 of T47D cells were seeded to each well of a 96-well cell culture plate and maintained at 37° C. and 5% $CO_2$ in a cell culture incubator overnight. On the day of experiment, cell culture medium was removed. 180 µl of fresh medium containing 100 nM MMS (Sigma) was added to each well and followed by 20 µl medium containing 10 folds of the concentrations of experimental drugs or reference compound (ADZ2281 and ABT-888). The serial dilutions of the compounds to be tested and the reference compounds were made in a 1:3 and 1:10 fashion in DMSO. The 10-fold compound solutions were made by mixing 10 µl DMSO serial dilution solutions with 90 µl fresh growth medium. Twenty four hours later, the cells in the 96-well plates were centrifuged at 1000 g for 5 min and the supernatants were removed. 50 µl lysis buffer (10 mM Tris, pH 7.5, 0.1 M NaCl, 1 mM EDTA, 0.01% Triton X-100) was added to each well and the plates were shaked horizontally for 30 min at 4° C. After centrifugation at 1000 g at 4° C. for 10 min, 20 µl of supernatant was transferred from each well to a corresponding well in a 384-well black plate. 20 µl of buffer (20 mM PIPES, pH 7.4, 4 mM EDTA and 0.2% CHAPS) containing 20 µM fluorescent caspase-3 substrate ((Ac-DEVD)$_2$-R110, AnaSpec Cat #60304-5) was added to each well afterwards. The plates were shaked to uniformly mix the wells and incubated at 37° C. for 3 h. The fluorescence intensity was measured using the following wavelength: ex: 496 nm, em: 520 nm using a fluorescence plate reader (Varioskan Flash, Thermo Fisher Scientific). The caspase-3 activity induced by the compounds was expressed as a relative fluorescence unit (RFU). The obtained fluorescence readings were analyzed using a commercial graphic software (GraphPad Prism 5) and plotted against the Log value of the compound concentrations. The $EC_{50}$ values were obtained by fitting the data points with the equation of Y (fluorescence reading)=minimal fluorescence reading+(maximal fluorescence reading−minimal fluorescence reading)/(1+10^(Log$EC_{50}$−LogC)), where C is the concentration of the testing compound. The $EC_{50}$ values were obtained by fitting the data points with S-shaped dose response curve equation (GraphPad Software, Inc). The synergistic potentiation effect of compounds on MMS induced apoptosis in cells is expressed as $EC_{50}$ values and listed in Table 2.

TABLE 2

| Compounds potentiate the apoptosis inducing activity of MMS ($EC_{50}$) | | | | | | | |
|---|---|---|---|---|---|---|---|
| Example | 5 | 6 | 7 | 8 | 9 | 10 | 11 | 12 |
| $IC_{50}$ (nM) | 3.5 | >1000 | 62 | 20 | 91 | 325 | 31 | 62 |
| Example | 13 | 14 | 15 | 16 | 18 | 19 | 20 | 21 |
| $IC_{50}$ (nM) | 374 | 35 | 72 | 43 | 41 | 324 | 0.99 | 2.8 |
| Example | 22 | 23 | 24 | 25 | 26 | 27 | 28 | 29 |
| $IC_{50}$ (nM) | 2.8 | 1.6 | 9.9 | 6.2 | 5.6 | 58 | 14 | 138 |
| Example | 30 | 31 | 32 | 33 | 34 | 35 | 36 | 37 |
| $IC_{50}$ (nM) | 32 | 295 | 27 | 187 | 402 | 12 | 13 | 48 |
| Example | 38 | 39 | 41 | 42 | 45 | AZD2281 | |
| $IC_{50}$ (nM) | 25 | 32 | 2.2 | 4.0 | 402 | 14 | |

Therefore, as measured 1-(3-(4-(pyrimidin-2-yl)piperazine-1-carbonyl)benzyl)-5,6,7,8-tetrahydroquinazoline-2,4 (1H, 3H)-dione (Example 5) and its analogs have shown excellent potentiation effect on DNA damaging anticancer drug such as MMS induced cancer cell apoptosis. Compounds of Example 5, 18, and 20 were found to be 5-10 folds more active than reference compound AZD2281.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:
1. A compound having the Formula III:

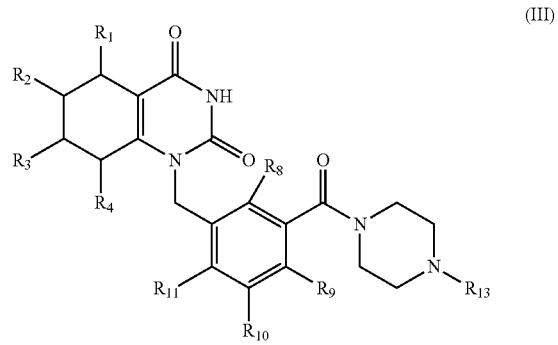

or a pharmaceutically acceptable salt thereof, wherein:

$R_1$-$R_4$ independently are hydrogen, halo, optionally substituted amino, optionally substituted alkoxy, optionally substituted $C_{1-10}$ alkyl, haloalkyl, alkenyl, alkynyl, hydroxyalkyl, aminoalkyl, carboxyalkyl, nitro, cyano, ethylenedioxo, $C_{1-6}$ alkanoylamido, hydroxy, thiol, $C_{1-6}$ alkanoyloxy, azido, carboxy, carbonylamido or optionally substituted alkylthiol; and $R_8$, $R_9$, $R_{10}$, and $R_{11}$ are hydrogen or fluoro; $R_{13}$ is optionally substituted cycloalkyl, aryl, heteroaryl, heterocyclic group, arylalkyl, heteroarylalkyl, carbocycloalkyl, alkylcarbonyl, cycloalkylcarbonyl, arylcarbonyl, heteroarylcarbonyl or heterocyclocarbonyl.

2. A compound selected from the group consisting of:

1-(3-(4-(Pyrimidin-2-yl)piperazine-1-carbonyl)benzyl)-5,6,7,8-tetrahydroquinazoline-2,4(1H, 3H)-dione;

1-(3-(4-(Cyclopropylcarbonyl)piperazine-1-carbonyl)benzyl)-5,6,7,8-tetrahydroquinazoline-2,4(1H, 3H)-dione;

1-(3-(4-(Thiophene-2-carbonyl)piperazine-1-carbonyl)benzyl)-5,6,7,8-tetrahydroquinazoline-2,4(1H, 3H)-dione;

1-(3-(4-(Thiazol-2-yl)piperazine-1-carbonyl)benzyl)-5,6,7,8-tetrahydroquinazoline-2,4(1H, 3H)-dione;

1-(3-(4-(Cyclopentylcarbonyl)piperazine-1-carbonyl)benzyl)-5,6,7,8-tetrahydroquinazoline-2,4(1H, 3H)-dione;

1-(3-(4-Benzoylpiperazine-1-carbonyl)benzyl)-5,6,7,8-tetrahydroquinazoline-2,4(1H, 3H)-dione;

1-(3-(4-(Pyridin-2-yl)piperazine-1-carbonyl)benzyl)-5,6,7,8-tetrahydroquinazoline-2,4(1H, 3H)-dione;

1-(3-(4-(Cyclohexylcarbonyl)piperazine-1-carbonyl)benzyl)-5,6,7,8-tetrahydroquinazoline-2,4(1H, 3H)-dione;

1-(3-(4-(Furan-2-carbonyl)piperazine-1-carbonyl)benzyl)-5,6,7,8-tetrahydroquinazoline-2,4(1H, 3H)-dione;

1-(3-(4-(Cyclobutylcarbonyl)piperazine-1-carbonyl)benzyl)-5,6,7,8-tetrahydroquinazoline-2,4(1H, 3H)-dione;

1-(3-(4-(Thiophene-3-carbonyl)piperazine-1-carbonyl)benzyl)-5,6,7,8-tetrahydroquinazoline-2,4(1H, 3H)-dione;

1-(3-(4-(Pyrazin-2-yl)piperazine-1-carbonyl)benzyl)-5,6,7,8-tetrahydroquinazoline-2,4(1H, 3H)-dione;

1-(4-Fluoro-3-(4-benzoylpiperazine-1-carbonyl)benzyl)-5,6,7,8-tetrahydroquinazoline-2,4(1H,3H)-dione;

1-(4-Fluoro-3-(4-(cyclopropylcarbonyl)piperazine-1-carbonyl)benzyl)-5,6,7,8-tetrahydroquinazoline-2,4(1H, 3H)-dione;

1-(4-Fluoro-3-(4-(pyrimidin-2-yl)piperazine-1-carbonyl)benzyl)-5,6,7,8-tetrahydroquinazoline-2,4(1H,3H)-dione;

1-(4-Fluoro-3-(4-(thiophene-2-carbonyl)piperazine-1-carbonyl)benzyl)-5,6,7,8-tetrahydroquinazoline-2,4(1H,3H)-dione;

1-(4-Fluoro-3-(4-(cyclobutylcarbonyl)piperazine-1-carbonyl)benzyl)-5,6,7,8-tetrahydroquinazoline-2,4(1H, 3H)-dione;

1-(4-Fluoro-3-(4-(thiazol-2-yl)piperazine-1-carbonyl)benzyl)-5,6,7,8-tetrahydroquinazoline-2,4(1H, 3H)-dione;

1-(4-Fluoro-3-(4-(cyclohexylcarbonyl)piperazine-1-carbonyl)benzyl)-5,6,7,8-tetrahydroquinazoline-2,4(1H, 3H)-dione;

1-(4-Fluoro-3-(4-(cyclopentylcarbonyl)piperazine-1-carbonyl)benzyl)-5,6,7,8-tetrahydroquinazoline-2,4(1H, 3H)-dione;

1-(4-Fluoro-3-(4-(pyridin-2-yl)piperazine-1-carbonyl)benzyl)-5,6,7,8-tetrahydroquinazoline-2,4(1H, 3H)-dione;

1-(4-Fluoro-3-(4-(furan-2-carbonyl)piperazine-1-carbonyl)benzyl)-5,6,7,8-tetrahydroquinazoline-2,4(1H, 3H)-dione;

1-(4-Fluoro-3-(4-(pyrazin-2-yl)piperazine-1-carbonyl)benzyl)-5,6,7,8-tetrahydroquinazoline-2,4(1H, 3H)-dione;

1-(4-Fluoro-3-(4-ethylsulfonylpiperazine-1-carbonyl)benzyl)-5,6,7,8-tetrahydroquinazoline-2,4(1H, 3H)-dione;

1-(4-Fluoro-3-(4-cyclohexylpiperazine-1-carbonyebenzyl)-5,6,7,8-tetrahydroquinazoline-2,4(1H, 3H)-dione;

1-(4-Fluoro-3-(4-ethylpiperazine-l-carbonyl)benzyl)-5,6,7,8-tetrahydroquinazoline-2,4(1H,3H)-dione;

1-(4-Fluoro-3-(4-(4-fluorobenzoyl)piperazine-1-carbonyl)benzyl)-5,6,7,8-tetrahydroquinazoline-2,4(1H, 3)-dione;

1-(4-Fluoro-3-(4-phenylpiperazine-1-carbonyl)benzyl)-5,6,7,8-tetrahydroquinazoline-2,4(1H, 3H)-dione;

1-(4-Fluoro-3-(4-acetylpiperazine-1-carbonyl)benzyl)-5,6,7,8-tetrahydroquinazoline-2,4(1H, 3H)-dione;

1-(4-Fluoro-3-(4-(furan-3-carbonyppiperazine-1-carbonyl)benzyl)-5,6,7,8-tetrahydroquinazoline-2,4(1H, 3H)-dione;

1-(4-Fluoro-3-(4-(thiophene-3-carbonyl)piperazine-1-carbonyl)benzyl)-5,6,7,8-tetrahydroquinazoline-2,4 (1H, 3H)-dione;

1-(4-Fluoro-3-(4-(4-methoxybenzoyl)piperazine-1-carbonyl)benzyl)-5,6,7,8-tetrahydroquinazoline-2,4(1H, 3H)-dione;

1-(4-Fluoro-3-(4-(cyclohexylmethyl)piperazine-1-carbonyl)benzyl)-5,6,7,8-tetrahydroquinazoline-2,4(1H, 1H)-dione;

1-(4-Fluoro-3-(4-(tetrahydrofuran-2-carbonyl)piperazine-1-carbonyl)benzyl)-5,6,7,8-tetrahydroquinazoline-2,4(1H,3H)-dione;

1-(6-Fluoro-3-(4-(pyrimidin-2-yl)piperazine-1-carbonyl)benzyl)-5,6,7,8-tetrahydroquinazoline-2,4(1H, 3H)-dione;

1-(6-Fluoro-3-(4-(cyclopentylcarbonyl)piperazine-l-carbonyl)benzyl)-5,6,7,8-tetrahydroquinazoline-2,4(1H, 3H)-dione;

1-(3-(4-(pyrimidin-2-yl)piperazine-1-carbonyl)benzyl)-6,7-dihydro-1H-cyclopenta[d]pyrimidine-2,4(3H, 5H)-dione;

1-(6-Fluoro-3-(4-(thiophene-3-carbonyl)piperazine-1-carbonyl)benzyl)-5,6,7,8-tetrahydroquinazoline-2,4 (1H, 3H)-dione;

1-(6-Fluoro-3-(4-(pyridin-2-yl)piperazine-1-carbonyl)benzyl)-5,6,7,8-tetrahydroquinazoline-2,4(1H, 3H)-dione;

1-(6-Fluoro-3-(4-benzoylpiperazine-1-carbonyl)benzyl)-5,6,7,8-tetrahydroquinazoline-2,4(1H, 3H)-dione;

1-(6-Fluoro-3-(4-(cyclohexylcarbonyl)piperazine-1-carbonyl)benzyl)-5,6,7,8-tetrahydroquinazoline-2,4(1H, 3H)-dione;

1-(6-Fluoro-3-(4-(cyclobutylcarbonyl)piperazine-1-carbonyl)benzyl)-5,6,7,8-tetrahydroquinazoline-2,4(1H, 3H)-dione;

1-(6-Fluoro-3-(4-(thiazol-2-yl)piperazine-1-carbonyl)benzyl)-5,6,7,8-tetrahydroquinazoline-2,4(1H, 3H)-dione;

1-(6-Fluoro-3-(4-(furan-2-carbonyl)piperazine-1-carbonyl)benzyl)-5,6,7,8-tetrahydroquinazoline-2,4(1H, 3H)-dione;

1-(4-Fluoro-3-(4-(tetrahydro-2H-pyran-4-carbonyl)piperazine-1-carbonyl)benzyl)-5,6,7,8-tetrahydroquinazoline-2,4(1H, 3H)-dione;

1-(4-Fluoro-3-(4-phenylpiperidine-1-carbonyl)benzyl)-5,6,7,8-tetrahydroquinazoline-2,4(1H, 3H)-dione;

1-(4-Fluoro-3-(4-(pyrimidin-2-yl)piperazine-1-carbonyl)benzyl)-6-methyl-5,6,7,8-tetrahydroquinazoline-2,4(1H, 3H)-dione;

1-(4-Fluoro-3-(4-(pyridin-2-yl)piperazine-1-carbonyl)benzyl)-5-methyl-5,6,7,8-tetrahydroquinazoline-2,4(1H, 3H)-dione; and 1-(4-Fluoro-3-(4-(pyrimidin-2-yl)piperazine-1-carbonyl)benzyl)-6,7,8,9-tetrahydro-1H-cyclohepta[d]pyrimidine-2,4(3H, 5H)-dione;

or a pharmaceutically acceptable salt thereof.

3. A pharmaceutical composition comprising the compound of claim 1 and a pharmaceutically acceptable carrier.

* * * * *